(12) United States Patent
Duffy et al.

(10) Patent No.: US 6,641,815 B2
(45) Date of Patent: Nov. 4, 2003

(54) SEQUESTRIN

(75) Inventors: Patrick E. Duffy, Nairobi (KE); Christian F. Ockenhouse, Burtonsville, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 09/351,794

(22) Filed: Jul. 13, 1999

(65) Prior Publication Data

US 2002/0042382 A1 Apr. 11, 2002

Related U.S. Application Data

(62) Division of application No. 08/559,896, filed on Nov. 17, 1995, now Pat. No. 6,310,046.

(51) Int. Cl.$^7$ .................. A61K 39/00; A61K 39/002
(52) U.S. Cl. .................. 424/191.1; 530/300; 530/327; 530/328; 530/350
(58) Field of Search .................. 435/440, 252.3, 435/254.11, 325, 320.1; 536/23.1, 23.5; 514/44; 530/350, 300, 328, 327; 424/184.1, 185.1, 191.1, 269.1, 265.1, 272.1

(56) References Cited

U.S. PATENT DOCUMENTS

| | | | | |
|---|---|---|---|---|
| 4,464,394 A | * | 8/1984 | Bollag | 424/317 |
| 5,589,466 A | * | 12/1996 | Felgner et al. | 514/44 |
| 5,593,972 A | * | 1/1997 | Weiner et al. | 514/44 |

FOREIGN PATENT DOCUMENTS

WO  WO 97/19168  *  5/1997

OTHER PUBLICATIONS

Sigma Catalog, 1988, pp. 1662–1663.*

Reiger et al in "Glossary of Genetics and Cytogenetics", Springer–Verlag p 17–18, 1976.*

Ockenhouse et al. Idenfification of a Platelet Membrane Glycoprotein as a Falciparum Malaria Sequestration Receptor; Mar. 17, 1989; Science 243:1469–1471.*

Ockenhouse et al. Sequestrin, a CD36 recognition protein on Plasmodium falciparum malaria–infected by anti–idiotype antibodies; Proc.Nail.acad. Sci. USA; vol. 88, pp. 3175–3179, Apr. 1991; Medical Sciences.*

Donald J. Krogstad; Malaria as a Reemerging Disease; Epidemiologic Reviews; vol. 18, No. 1, published Sep. 1996; pp. 77–89.*

Juha Partanen; A Novel Endothelial Cell Surface receptor Tyrosin Kinase with Extracellular Epidermal Growth Factor Homology Domains; Molecular and Cellular Biology, vol. 12, No. 4, Apr., 1992, pp. 1698–1707.*

* cited by examiner

*Primary Examiner*—Patricia A. Duffy
(74) *Attorney, Agent, or Firm*—Elizabeth Arwine; Charles H. Harris

(57) ABSTRACT

In this application is described the expression cloning and functional characterization of the CD36-binding domain of Sequestrin. Sequestrin is a surface protein of 215–250 kD size which does not vary in size between parasite strains. The Sequestrin gene appears to be single-copy-number within the genome; noncytoadherent laboratory parasite strains carry the sequestrin gene but fail to express the protein. Sequestrin binds with high affinity to CD36. Sequestrin protein and sequence can be used as a diagnostic, prognostic, and therapeutic tool.

14 Claims, 11 Drawing Sheets

SEQUENCE LISTING

<160> NUMBER OF SEQ ID NOS: 7

<210> SEQ ID NO 1
<211> LENGTH: 1956
<212> TYPE: DNA
<213> ORGANISM: Plasmodium falciparum

<400> SEQUENCE: 1

```
gaagagctga agaaaaaaaa ggaaaataca aacacaaata caaatacaag tacaaataca      60
agtgcaaata caaatacaag tacaaacaca agtgcaaaca caaatacaag tacaaagaa     120 tctcacatat tagatgaatc gaaactagaa accttttaca gagacgaatt agacaaaatg    180
```

-continued

```
ggaaaagaag aaattgaaac atatttcaaa gggaatattg acaaaaaatc acttgatgaa      240
tttcataaaa tattgctaga gagttaaac aaaatggaca agatgaatt atatgaaatg        300 tatagagaag agttaaatag gattgaacaa gaaaaaatta gaaatatgaa taagaagaa       360 ataaataaaa cttacaagga cgaaataaat aatatgaata gtgatcaagt tgataaaata      420
catagagaag aattagaaaa aatcgaaaaa gaaaaaataa acaaaatgga taagatgaa       480 atagataaaa tatatagaga gaattagac aaaatggatc gagatgcaat ttatagtatg       540
tatatagaag atataagtaa caaaaatata aaagacttaa ttaaaaatga aaggaaaca       600 aataaggata aaacaaaaa aaagatata gatataaaca aaagaaaaa aaagatata          660 gatatagatg tagacataga taaagatata cataaagatc atgtagaaga attatacgga      720
gaagtaaaaa acaaacttag caaagaagaa ttagatagaa tggacagaga cgcattatat      780
agagtatacc tagaagaatt agatagaatg aacagagacg aattatatag agtataccta     840
gaagaattag aaaaaataga caaggaagaa aaagaaaaaa ttcatagaga aaaattacac      900
aaaattgaaa aagagaaaat aaataaaatg gataaagatc aaatagataa aatatatgaa      960
gaagaattaa acaaaatgga tagtgatgaa attcaacatg taaggagagc aatattacaa     1020
gatatacaaa aagaaaaaat acaaaattta gaactagaag aaatcgatag acttataaa      1080 gaagaattag atagaatgga tagagaagca aggtatgaaa tccccatgag aaatttaagc     1140
agaaatgaaa aagataatat tatacataga aatattaaaa atgaatctaa ccaaaaaaat     1200
aagaaagaaa atgtaaatgt atttataata cacgacaata atgatagtaa taataataat     1260
aataataata atagagatgt gaataattta aataataagc acacaaataa taattataat     1320
gaaaatgtag aagttgaatt agttgtacga aatttagaca aggataaagg agccaagata     1380
gaagatatta tagactattt taacaaagaa attaaaaag acaaaaatgt taatgtttcc      1440
aatatagtga atttttaaa ttcaaaagta ggaaagata acacaccaat tcaacataag       1500
aaggaaaatc aagtagatgt tgtcaggaaa aatattcaga ttattcaaga ggataatata     1560
aaaaataaag gccaaaagga taacactgaa atgttagata ataataagga aataacaaat     1620
attgatataa aaatgttga tgatataaaa aatgttggag atataaaaag tgttggagat     1680
ataaaaagtg ttgatgatat aaacaatgtt gatggtataa aaaatgttga tggtataaaa     1740
aatgttgatg gtataaaaaa tgttgatggt ataaacaatg tgggagatat aaacaatgct     1800
ggagatacaa ataatgctgg agatataaac aatgtgggcg atataaacaa ttctgtagat     1860
atatacaacg ttgaacatat agacgaagcg gagaaaaaac caaatcttga taatccaaaa     1920
aagtttgact ggacacaggt atttaaagac aaagta                                1956
```

<210> SEQ ID NO 2
<211> LENGTH: 652
<212> TYPE: PRT
<213> ORGANISM: Plasmodium falciparum

<400> SEQUENCE: 2

```
Glu Glu Leu Lys Lys Lys Lys Glu Asn Thr Asn Thr Asn Thr Asn Thr
 1               5                   10                  15

Ser Thr Asn Thr Ser Ala Asn Thr Asn Thr Ser Thr Asn Thr Ser Ala
                20                  25                  30

Asn Thr Asn Thr Ser Thr Lys Glu Ser His Ile Leu Asp Glu Ser Lys
            35                  40                  45

Leu Glu Thr Phe Tyr Arg Asp Glu Leu Asp Lys Met Gly Lys Glu Glu
        50                  55                  60
```

-continued

```
Ile Glu Thr Tyr Phe Lys Gly Asn Ile Asp Lys Lys Ser Leu Asp Glu
 65                  70                  75                  80

Phe His Lys Ile Leu Leu Glu Glu Leu Asn Lys Met Asp Lys Asp Glu
                 85                  90                  95

Leu Tyr Glu Met Tyr Arg Glu Glu Leu Asn Arg Ile Glu Gln Gln Lys
                100                 105                 110

Ile Arg Asn Met Asn Lys Gln Gln Ile Asn Lys Thr Tyr Lys Asp Glu
            115                 120                 125

Ile Asn Asn Met Asn Ser Asp Gln Val Asp Lys Ile His Arg Glu Glu
        130                 135                 140

Leu Glu Lys Ile Glu Lys Glu Lys Ile Asn Lys Met Asp Lys Asp Glu
145                 150                 155                 160

Ile Asp Lys Ile Tyr Arg Glu Glu Leu Asp Lys Met Asp Arg Asp Ala
                165                 170                 175

Ile Tyr Ser Met Tyr Ile Glu Asp Ile Ser Asn Lys Asn Ile Lys Asp
                180                 185                 190

Leu Ile Lys Asn Glu Lys Glu Thr Asn Lys Asp Lys Asn Lys Lys Lys
            195                 200                 205

Asp Ile Asp Ile Asn Lys Lys Lys Lys Asp Ile Asp Ile Asp Val
        210                 215                 220

Asp Ile Asp Lys Asp Ile His Lys Asp His Val Glu Glu Leu Tyr Gly
225                 230                 235                 240

Glu Val Lys Asn Lys Leu Ser Asp Glu Glu Leu Asp Arg Met Asp Arg
                245                 250                 255

Asp Ala Leu Tyr Arg Val Tyr Leu Glu Glu Leu Asp Arg Met Asn Arg
                260                 265                 270

Asp Glu Leu Tyr Arg Val Tyr Leu Glu Glu Leu Glu Lys Ile Asp Lys
            275                 280                 285

Glu Glu Lys Glu Lys Ile His Arg Glu Lys Leu His Lys Ile Glu Lys
        290                 295                 300

Glu Lys Ile Asn Lys Met Asp Lys Asp Gln Ile Asp Lys Ile Tyr Glu
305                 310                 315                 320

Glu Glu Leu Asn Lys Met Asp Ser Asp Glu Ile Gln His Val Arg Arg
                325                 330                 335

Ala Ile Leu Glu Asp Ile Gln Lys Glu Lys Ile Gln Asn Leu Glu Leu
                340                 345                 350

Glu Glu Ile Asp Arg Leu Tyr Lys Glu Glu Leu Asp Arg Met Asp Arg
            355                 360                 365

Glu Ala Arg Tyr Glu Ile Pro Met Arg Asn Leu Ser Arg Asn Glu Lys
        370                 375                 380

Asp Asn Ile Ile His Arg Asn Ile Lys Asn Glu Ser Asn Gln Lys Asn
385                 390                 395                 400

Lys Lys Glu Asn Val Asn Val Phe Ile Ile His Asp Asn Asn Asp Ser
                405                 410                 415

Asn Asn Asn Asn Asn Asn Asn Arg Asp Val Asn Asn Leu Asn Asn
                420                 425                 430

Lys His Thr Asn Asn Asn Tyr Asn Glu Asn Val Glu Val Glu Leu Val
            435                 440                 445

Val Arg Asn Leu Asp Lys Asp Lys Gly Ala Lys Ile Glu Asp Ile Ile
        450                 455                 460

Asp Tyr Phe Asn Lys Glu Ile Lys Lys Asp Lys Asn Val Asn Val Ser
465                 470                 475                 480
```

```
Asn Ile Val Asn Phe Leu Asn Ser Lys Val Gly Lys Asp Asn Thr Pro
                485                 490                 495

Ile Gln His Lys Lys Glu Asn Gln Val Asp Val Arg Lys Asn Ile
            500                 505                 510

Gln Ile Ile Gln Glu Asp Asn Ile Lys Asn Lys Gly Gln Lys Asp Asn
            515                 520                 525

Thr Glu Met Leu Asp Asn Lys Glu Ile Thr Asn Ile Asp Ile Lys
        530                 535                 540

Asn Val Asp Asp Ile Lys Asn Val Gly Asp Ile Lys Ser Val Gly Asp
545                 550                 555                 560

Ile Lys Ser Val Asp Asp Ile Asn Asn Val Asp Gly Ile Lys Asn Val
                565                 570                 575

Asp Gly Ile Lys Asn Val Asp Gly Ile Lys Asn Val Asp Gly Ile Asn
            580                 585                 590

Asn Val Gly Asp Ile Asn Asn Ala Gly Asp Thr Asn Asn Ala Gly Asp
            595                 600                 605

Ile Asn Asn Val Gly Asp Ile Asn Asn Ser Val Asp Ile Tyr Asn Val
        610                 615                 620

Glu His Ile Asp Glu Ala Glu Lys Lys Pro Asn Leu Asp Asn Pro Lys
625                 630                 635                 640

Lys Phe Asp Trp Thr Gln Val Phe Lys Asp Lys Val
                645                 650

<210> SEQ ID NO 3
<211> LENGTH: 417
<212> TYPE: DNA
<213> ORGANISM: Plasmodium falciparum

<400> SEQUENCE: 3
cacatattag atgaatcgaa actagaaacc ttttacagag acgaattaga caaaatggga      60
aaagaagaaa ttgaaacata tttcaaaggg aatattgaca aaaaatcact tgatgaattt     120
cataaaatat tgctagaaga gttaaacaaa atggacaaag atgaattata tgaaatgtat     180
agagaagagt taaataggat tgaacaagaa aaaattagaa atatgaataa gaagaaata      240 aataaaactt acaaggacga aataaataat atgaatagtg atcaagttga taaaatacat     300
agagaagaat tagaaaaaat cgaaaaagaa aaaataaaca aaatggataa agatgaaata     360
gataaaatat atagagaaga attagacaaa atggatcgag atgcaattta tagtatg        417

<210> SEQ ID NO 4
<211> LENGTH: 139
<212> TYPE: PRT
<213> ORGANISM: Plasmodium falciparum

<400> SEQUENCE: 4

His Ile Leu Asp Glu Ser Lys Leu Glu Thr Phe Tyr Arg Asp Glu Leu
  1               5                  10                  15

Asp Lys Met Gly Lys Glu Glu Ile Glu Thr Tyr Phe Lys Gly Asn Ile
             20                  25                  30

Asp Lys Lys Ser Leu Asp Glu Phe His Lys Ile Leu Leu Glu Glu Leu
         35                  40                  45

Asn Lys Met Asp Lys Asp Glu Leu Tyr Glu Met Tyr Arg Glu Glu Leu
     50                  55                  60

Asn Arg Ile Glu Gln Gln Lys Ile Arg Asn Met Asn Lys Gln Gln Ile
 65                  70                  75                  80

Asn Lys Thr Tyr Lys Asp Glu Ile Asn Asn Met Asn Ser Asp Gln Val
```

```
                         85                  90                  95
Asp Lys Ile His Arg Glu Glu Leu Glu Lys Ile Glu Lys Glu Lys Ile
                100                 105                 110
Asn Lys Met Asp Lys Asp Glu Ile Asp Lys Ile Tyr Arg Glu Glu Leu
        115                 120                 125
Asp Lys Met Asp Arg Asp Ala Ile Tyr Ser Met
    130                 135

<210> SEQ ID NO 5
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Asp Glu Phe His Lys Ile Leu Leu Glu Glu Leu Asn Lys Met Asp Lys
 1               5                  10                  15

Asp Glu Leu

<210> SEQ ID NO 6
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Asn Leu Glu Leu Glu Glu Ile Asp Arg Leu Tyr Lys Glu Glu Leu Asp
 1               5                  10                  15

<210> SEQ ID NO 7
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Tyr Leu Glu Glu Leu Glu Lys Ile Asp Lys Glu Glu Lys Glu Lys Ile
 1               5                  10                  15
```

SEQUESTRIN

This application is a divisional application of U.S. application Ser. No. 08/559,896, filed Nov. 17, 1995, now U.S. Pat. No. 6,310,046.

INTRODUCTION

Alone among the malaria species which infect humanity, *Plasmodium falciparum* causes the erythrocytes which it invades to sequester in the deep vascular beds of various tissues. This sequestration phenomenon is observed in peripheral blood smears by the presence of immature (non-adherent) ring-stage parasitized erythrocytes and the absence of mature (adherent) trophozoite and schizont stage parasites, the latter having localized to postcapillary venules (Bignami and Bastianeli (1889) *Reforma Medica* 6: 1334–1335) (All documents cited herein supra and infra are hereby incorporated by reference). Sequestration allows the parasite to develop in a microenvironment of low oxygen tension and to evade splenic immune surveillance (Langreth and Peterson (1985) *Infect. Immun.* 47: 760–766).

*Faliparcum malaria* can have protean manifestations, ranging from asymptomatic infection, to mild disease (symptoms may include fever, arthralgias, abdominal pain, diarrhea, headache, nausea, fatigue and others in various combinations), to severe disease (recognized severe forms include cerbral malaria with coma, pulmonary edema with consequent resperiatory failure, severe anemia with consequent hemodynamic/cardiopulmonary decompensation) often resulting in death. These symptoms of severe malaria resulting in vast mortality worldwide are believed to be imparted by sequestration (Warrell et al. (1990) *Trans. Soc. Trop. Med. Hyg.* 84:1–65). Owing to the devastating consequences of the disease, and the potential for therapeutic intervention, researchers have long sought to isolate the parasite protein(s) responsible for the cytoadherence of *P. falciparum* infected erythrocytes (IRBC) to postcapillary venular endothelium.

Cytoadherence appears to be a complex event, with multiple binding phenotypes displayed by both culture-adapted and wild-type IRBC isolates. In vitro models demonstrate that different cell lines, such as C32 amelanotic melanoma cells (Schmidt et al. (1982) *J. Clin. Invest.* 70: 379–386), human umbilical vein (Udeinya et al. (1981) *Nature* 303: 429–431) and human microvascular endothelial cells (Johnson et al. (1993) *J. Infect. Dis.* 167: 698–703) support adhesion of IRBC. More recently, with the availability of purified molecules, an array of endothelial ligands such as CD36 (Ockenhouse et al. (1989)*Science* 243: 1469–1471) ICAM-1 (Berendt et al. (1989) *Nature* 341: 57–59) VCAM-1 (Ockenhouse et al. (1992) *J. Exp. Med.* 176: 1183–1189), E-selectin (Ockenhouse et al., 1992), and the extracellular matrix molecules thrombospondin (Roberts et al., year, *Nature* 318: 64–66) and chondroitan sulfate A (Rogerson et al. (1995) *J. Exp. Med.* 182:15–70) have demonstrated the capacity to bind IRBC. While culture-adapted IRBC can be selected to bind each of these ligands, only CD36 is able to bind nearly all wild-type parasite strains isolated in the field (Ockenhouse et al (1991) *Proc. Natl. Acad. Sci. U.S.A.* 88:3175–b 3179); Hansen et al (1990) *Blood* 76: 1845–1852). Furthermore, *P. falciparum* parasites which no longer cytoadhere in vitro to cells expressing CD36, are unable to establish a virulent infection in primates, suggesting the primary role of sequestration for parasite survival (Langreth and Peterson, 1985, supra).

Electron microscopy studies have demonstrated that IRBC adherence to endothelium occurs along electron-dense protrusions, called "knobs", on the erythrocyte surface (MacPherson et al. (1985) *Am. J. Pathol.* 119: 385–401). The IRBC surface ligands for both CD36 and thrombospondin receptors have been localized to these knobs (Nakamura et al. (1992) *J. Histochem. Cytochem.* 40:1419–1422). Although culture-adapted laboratory parasites may bind CD36 in the absence of surface knobs, (Udomsangpetch et al. (1989) *Nature* 338: 763–765) the prevailing view is that the CD36-binding protein(s) localizes at the surface of the knob of all wild-type parasites.

CD36, an 88 kD glycoprotein expressed on the surface of microvascular endothelium, platelets, and monocytes belongs to a family of related proteins containing extensive amino acid homology (Greenwalt et al. (1992) *Blood* 80:1105–1115; Calvo et al. (1995) *Genoinics* 25: 100–106). Also known as platelet glycoprotein IV or IIIb, CD36 is expressed in a regulated fashion during cell development (Abumrad et al. (1993) *J. Biol. Chem.* 268: 17665–17668) and its expression is modulated by cytokines (Huh et al. (1995)*J. Biol. Chem.* 270: 6267–6271; Johnson et al. (1993) *J. Infect. Dis.* 167: 698–703). CD36 has binding sites for several molecules involved in hemostasis and atherogenesis, including collagen (Tandon et al. (1989) *J. Biol. Chem.* 264: 7570–7575), thrombospondin (Asch et al. (1992) *Biochem. Biophys. Res. Common.* 182: 1208–1217), oxidized low density lipoprotein (LDL) (Endemann et al. (1993)*J. Biol. Chem.* 268: 11811–11816), long chain fatty acids (Abumrad et al. (1993) supra), and anionic phospholipids (Rigotti et al. (1995)*J. Biol. Chem.* 270: 16221–16224).

Cytoadherence of IRBC in vitro can be inhibited or reversed by antibodies directed against either the surface of parasitized erythrocytes or against endothelial cell ligands. IRBC binding to CD36 is blocked by monoclonal antibodies OKM5 (Barnwell et al. (1985)*J. Immunol.* 135:3494–3497) and OKM8 (Ockenhouse et al., 1991) directed against discontinuous epitopes but not by other CD36 monoclonal antibodies which recognize linear continuous epitopes (Ockenhouse et al., unpublished observations) establishing the importance of conformationally-correct protein structure for IRBC binding to CD36. In monkeys, sequestration can be reversed by passive transfer of hyperimmune sera, leading to the clearance of IRBC in the spleen (David et al. (1983) *Proc. Natl. Acad. Sci. U.S.A.* 80: 5075–5079).

A number of parasite-derived and altered host proteins have been postulated to mediate IRBC cytoadherence. PfEMP1, a large molecular weight, size variable protein which is the product of the var gene family involved in malaria antigenic variation (Baruch et al., 1995; Su et al. (1995) *Cell* 82: 89–100; Smith et al., 1995), has characteristics which suggest its involvement in cytoadherence: PfEMP1 is expressed on the external erythrocyte surface as demonstrated by radioiodination and immunofluorescence; PfEMP1 is readily cleaved from the IRBC surface by proteolytic enzymes such as trypsin at concentrations known to abolish IRBC adhesion, and PfEMP1 varies its size in a manner which correlates with changes in both strain specificity and IRBC adhesion (Leech et al. (1984) *J. Exp. Med.* 159: 1567–1575; Baruch et al., 1995). Another candidate, band 3, is a surface protein of normal human erythrocytes which has been shown to be altered by malaria infection, exposing cryptic peptides in loops 3 and 7 (Crandall and Sherman (1994) *Parasitol.* 108:389–396). Monoclonal antibodies against altered band 3 inhibit cytoadherence in vitro (Crandall and Sherman, 1994) and synthetic peptides based on the cryptic epitopes of band 3 affect sequestration in vivo (Crandall et al. (1993) *Proc. Natl. Acad Sci. U.S.A.* 90:4703–4707).

A third candidate cytoadherent ligand, Sequestrin, was identified by immunoprecipitation of a high molecular weight (>200 kD) IRBC surface protein by anti-idiotype antibodies raised against the CD36-specific monoclonal antibody OKM8 (Ockenhouse et al., 1991). These monospecific, anti-idiotypic antibodies bound to the surface of IRBC and inhibited IRBC adhesion to CD36.

Cytoadherence, then, is critical to both the survival (Langreth and Peterson (1985) Infect. Immun. 47: 760–766) and pathology (Warrell et al., supra) of P. falciparum parasites, and is a multi-faceted process, involving a number of endothelial receptors, and one or more IRBC counter-receptors. Identifying IRBC counter-receptors has been an elusive goal of malaria research, possibly due to antigenic variation, immunologically cross-reactive proteins, or other mechanisms by which the parasite masks the presence of biologically vital adhesion protein(s) on the cell membrane. As well, the modalities for demonstrating an adhesion protein can be misleading; for example, an antibody which identifies a non-cytoadherent malaria protein can still inhibit adherence in a binding assay by causing IRBC agglutination.

The identification of an IRBC counter-receptor would allow for the design of anti-sequestration and anti-malaria agents, drugs and vaccines necessary for the prevention of cerebral malaria and the reduction of mortality from this disease worldwide.

SUMMARY

The complexity of the cytoadherence process led us to conclude that proof of a parasite-expressed counter-receptor must include binding of purified forms of the putative counter-receptor to a receptor, as well as competitive inhibition of IRBC binding to an endothelial receptor by the putative counter-receptor. In the absence of this direct evidence, data implicating a protein in cytoadherence can only be considered suggestive. We further employed this idea in our approach to isolating the Sequestrin gene, by using radiolabelled CD36 as a probe to identify clones from a P. falciparum cDNA expression library.

While it is theoretically possible that the use of anti-idiotypic antibody could be used to immunopurify Sequestrin from a lysiate of P. falciparum parasites, this approach is not technically feasible. Numerous approaches have been tried over the years to isolate the cytoadherence receptor. The approaches used have utilized antibodies to screen a cDNA library of P. falciparium. However, since a number of laboratories with many personnel have succeeded in isolating cDNA clones using this approach, they have been uniformly unsuccessful in isolating the parasite cytoadherence receptor. This is primarily because the parasite is promiscuous in the sense that many of the parasite's proteins cross react with each other because of similar amino acid motifs and redundant amino acid repeat units. Therefore, it is unlikely that the use of antibodies, including the use of anti-idiotype antibodies, to probe a cDNA library will yield a clone with properties for which one is searching. Two recent groups of researchers searching for the cytoadherence gene/protein have come up with alternative proteins (Pasloske et al. (1993) Mole. Biochem Parasitol. 59: 59–72; Barnes et al. (1995) Exp. Parasitol 81: 79–89). Due to these failures, we reasoned that the use of antibodies, whether anti-idiotypic or not, would not yield a positive malaria clone responsible for the binding to CD36. Instead, we used expression-cloning which utilizes receptor-counter-receptor recognition. In this approach we used CD36 to probe a cDNA library to isolate only those clone(s) which bind to CD36 thereby circumventing the possibility of getting a cross-reactive protein via the antibody selection technique. Only a single clone from 70,000 clones was isolated thus confirming the infrequency of positive selection utilizing expression-cloning yet confirming functional importance when the clone was sequenced and the Sequestrin protein expressed.

We report here direct evidence that Sequestrin is a high affinity receptor for CD36, and is distinct from both PfEMP1 and eythrocyte band 3. By expression cloning, we have obtained 2 kB of the nucleotide sequence for Sequestrin, and have used recombinant fusion protein studies to determine the CD36-binding domain of the protein.

Sequestrin is present and expressed in P. falciparum isolates which bind to CD36. Sequestrin is present in the genome of P. falciparum isolates which do not bind CD36; it is expressed in lower amounts, if at all, in laboratory isolates which do not bind, and levels of expression in field isolates which do not bind CD36 is currently unknown. Sequestrin is not present in the genome of P. vivax (as determined by PCR detection using primers based on the Sequestrin sequence). Therefore, DNA-based methods which detect Sequestrin in the genome of the parasite would be a technique to diagnose infections with P. falciparum malaria.

Therefore, it is an object of the present invention to provide a Sequestrin cDNA fragment encoding 1958 nucleotides useful as a diagnostic agent, a therapeutic agent, and a DNA-based vaccine.

It is another object of the invention to provide an amino acid sequence for Sequestrin protein encoding 652 amino acids.

It is another object of the invention to provide a recombinant vector comprising a vector and the above described DNA fragment.

It is a further object of the present invention to provide a host cell transformed with the above-described recombinant DNA construct.

It is another object of the present invention to provide a method for producing Sequestrin which comprises culturing a host cell under conditions such that the above-described DNA fragment is expressed and Sequestrin protein is thereby produced, and isolating Sequestrin protein for use as a vaccine and a diagnostic agent, and a therapeutic agent.

It is still another object of the invention to provide a purified Sequestrin protein useful as a vaccine against malaria and for detecting the presence of said disease in a suspected patient.

It is a further object of the present invention to provide an antibody to the above-described recombinant Sequestrin protein.

It is yet another object of the invention to provide a malaria vaccine effective for the production of antigenic and immunogenic response resulting in the protection of a mammal against malaria.

It is yet another object of the present invention to provide a method for the diagnosis of malaria comprising the steps of:

(i) contacting a sample from an individual suspected of having the disease with antibodies which recognize Sequestrin; and (ii) detecting the presence or absence of a complex formed between Sequestrin and antibodies specific therefor.

It is a further object of the present invention to provide a diagnostic kit comprising a recombinantly produced Sequestrin antibody and ancillary reagents suitable for use in detecting the presence Sequestrin in mammalian tissue or serum.

It is yet another object of the present invention to provide a method for the diagnosis of malaria from a sample using the polymerase chain reaction, said method comprising:

(I) extracting RNA from the sample;

(ii) converting the RNA into complementary DNA;

(iii) contacting said DNA with
  (a) at least four nucleotide triphosphates,
  (b) a primer that hybridizes to Sequestrin DNA, and
  (c) an enzyme with polynucleotide synthetic activity,
under conditions suitable for the hybridization and extension of said first primer by said enzyme, whereby a first DNA product is synthesized with said DNA as a template therefor, such that a duplex molecule is formed;

(iv) denaturing said duplex to release said first DNA product from said DNA;

(v) contacting said first DNA product with a reaction mixture comprising:
  (a) at least four nucleotide triphosphates,
  (b) a second primer that hybridizes to said first DNA, and
  (c) an enzyme with polynucleotide synthetic activity,
under conditions suitable for the hybridization and extension of said second primer by said enzyme, whereby a second DNA product is synthesized with said first DNA as a template therefor, such that a duplex molecule is formed;

(vi) denaturing said second DNA product from said first DNA product;

(vii) repeating steps iii–vi for a sufficient number of times to achieve linear production of said first and second DNA products;

(viii) fractionating said first and second DNA products generated from said Sequestrin DNA; and (ix) detecting said fractionated products for the presence or absence of Sequestrin in a sample.

It is yet another object of the present invention to provide a method for the detection of Sequestrin in a sample which comprises assaying for the presence or absence of Sequestrin RNA or DNA in a sample by hybridization assays.

It is an object of the present invention to provide a therapeutic method for the treatment or amelioration of symptoms of malaria, said method comprising providing to an individual in need of such treatment an effective amount of a Sequestrin antibody or an agent which inhibits Sequestrin expression or function in a pharmaceutically acceptable excipient.

BRIEF DESCRIPTION OF THE DRAWINGS

These and other features, aspects, and advantages of the present invention will become better understood with reference to the following description and appended claims, and accompanying drawings where:

DETAILED DESCRIPTION

Figure 1:
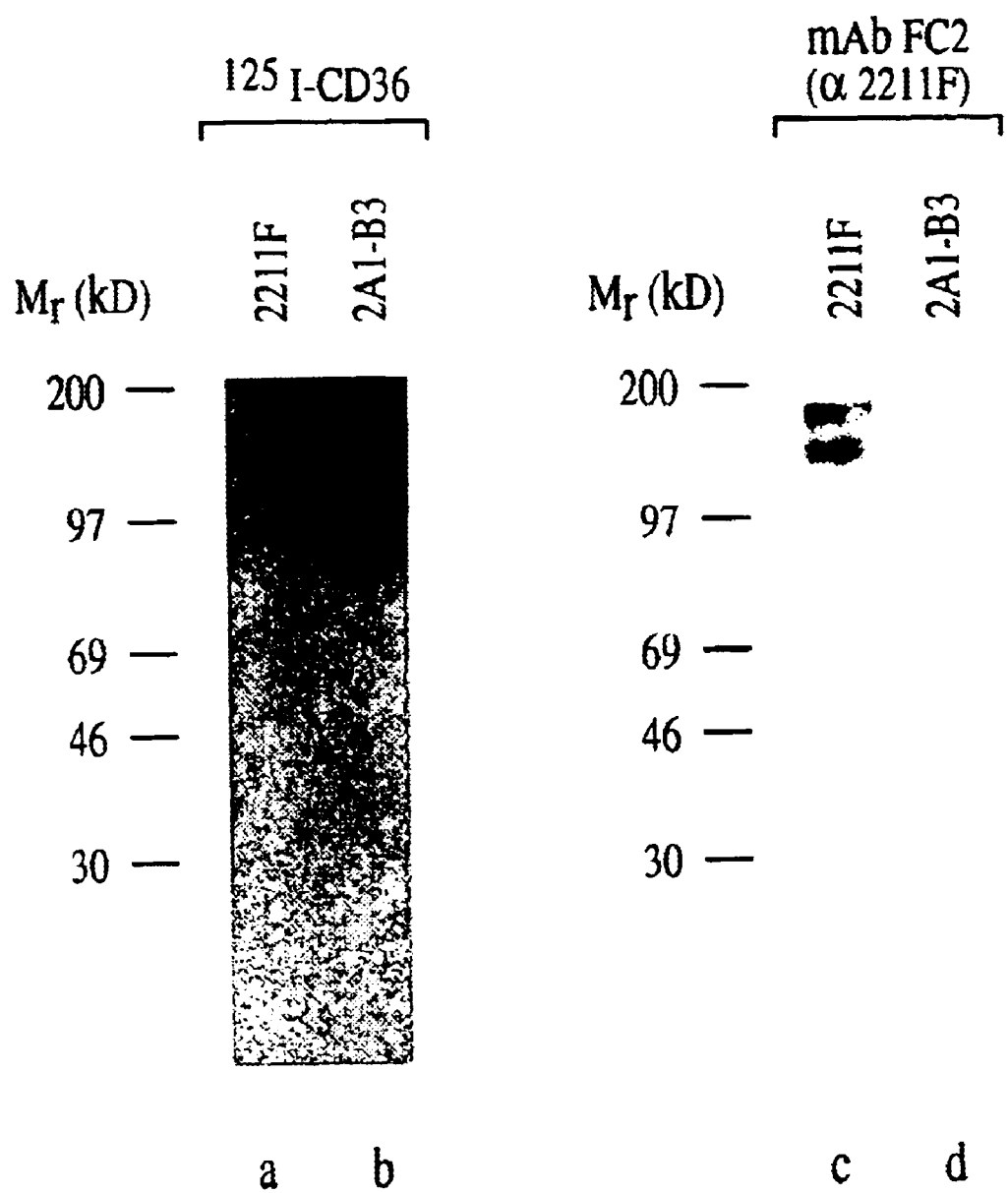
FIG. 1 demonstrates CD36 binding to β-galactosidase fusion protein of Sequestrin clone 2A1-B3. Affinity purified β-galactosidase fusion proteins 2A1-B3 and 2211F were separated by SDS-PAGE, transferred to nitrocellulose, and probed sequentially with Mab FC2 followed by $^{125}$I-CD36. A. Reactivity of Sequestrin clone 2A1-B3 with $^{125}$I-CD36 (lane 1) but not with control clone 2211F (lane 2). B. Immunoblotting of clones 2A1-B3 and 2211F with Mab FC2 identifies specific binding to clone 2211F(lane 4) but not to Sequestrin clone 2A1-B3 (lane 3). Bound antibodies were visualized by enhanced chemiluminescence (ECL).

In one embodiment, the present invention relates to a DNA or cDNA segment which encodes Sequestrin, a CD36-binding protein of *P. falciparum*. The sequence of the gene, specified in SEQ ID NO: 1, was obtained by sequencing a clone isolated by probing an expression library from *P. falciparum* with radiolabeled CD36. The sequenced gene fragment comprising 1958 nucleotides of open reading frame is A-T rich, a feature characteristic of other genes of malaria parasite origin.

DNA or polynucleotide sequences to which the invention also relates include sequences of at least about 6 nucleotides, preferably at least about 8 nucleotides, more preferably at least about 10–12 nucleotides, most preferably at least about 15–20 nucleotides corresponding, i.e., homologous to or complementary to, a region of the Sequestrin nucleotide sequence. Preferably, the sequence of the region from which the polynucleotide is derived is homologous to or complementary to a sequence which is unique to the Sequestrin gene. Whether or not a sequence is unique to the Sequestrin gene can be determined by techniques known to those of skill in the art. For example, the sequence can be compared to sequences in databanks, e.g., Genebank. Regions from which typical DNA sequences may be derived include but are not limited to, for example, regions encoding specific epitopes, for example the CD36-binding domain, as well as non-transcribed and/or non-translated regions.

The derived polynucleotide is not necessarily physically derived from the nucleotide sequence shown in SEQ ID NO: 1, but may be generated in any manner, including for example, chemical synthesis or DNA replication or reverse transcription or transcription, which are based on the information provided by the sequence of bases in the region(s) form which the polynucleotide is derived. In addition, combinations of regions corresponding to that of the designated sequence may be modified in ways known in the art to be consistent with an intended use. The sequences of the present invention can be used in diagnostic assays such as hybridization assays and polymerase chain reaction assays.

In addition the nucleotide sequence of the present invention can be used by someone with ordinary skill in the art to obtain the complete sequence of the Sequestrin gene by methods known in the art such as, for example, chromosome walking and cloning and sequencing overlapping cDNA or genomic DNA regions. The complete sequence of Sequestrin can be used as described above and is useful in diagnostic assays and in designing sequestration blocking agents.

DNA sequences to which the invention also relates include sequences which encode the specific protein epitopes or domains contained within said sequence which binds CD36. Specifically, such sequences include the nucleotide sequence encompassing from 140–555 specified as SEQ ID NO: 3, encoding a 139 amino acid CD36-binding domain specified as SEQ ID NO:4 or allelic forms which retain the ability to bind CD36. These sequences can be used to design anti-sequestration agents or to produce antibodies which inhibit sequestration in a mammal, such sequences and agents useful for amelioration or prevention of malaria disease symptoms.

In another embodiment, the present invention relates to a recombinant DNA molecule that includes a vector and a DNA sequence as described above (advantageously, a DNA sequence encoding the CD36 binding domain). The vector can take the form of a plasmid, or eukaryotic expression vector such as an n DNA vector, *Pichia pastoris*, or a virus vector virus such as for example, baculovirus vectors, retroviral vectors or adenoviral vectors, and others known in the art.

In a further embodiment, the present invention relates to host cells stably transformed or transfected with the above-described recombinant DNA constructs. The host cell can be prokaryotic (for example, bacterial), lower eukaryotic (for example, yeast or insect) or higher eukaryotic (for example, all mammals, including but not limited to mouse and human). Both prokaryotic and eukaryotic host cells may be used for expression of desired coding sequences when appropriate control sequences which are compatible with the designated host are used. Among prokaryotic hosts, *E. coli* is most frequently used. Expression control sequences for prokaryotes include promoters, optionally containing operator portions, and ribosome binding sites. Transfer vectors compatible with prokaryotic hosts are commonly derived from, for example, pBR322, a plasmid containing operons conferring ampicillin and tetracycline resistance, and the various pUC vectors, which also contain sequences conferring antibiotic resistance markers. These markers may be used to obtain successful transformants by selection.

Please see e.g., Maniatis, Fitsch and Sambrook, *Molecular Cloning: A Laboratory Manual* (1982) or *DNA Cloning*, Volumes I and II (D. N. Glover ed. 1985) for general cloning methods. The DNA sequence can be present in the vector operably linked to a highly purified IgG molecule, an adjuvant, a carrier, or an agent for aid in purification of Sequestrin, such as glutathione S-transferase. The recombinant molecule can be suitable for transfecting eukaryotic cells, for example, mammalian cells and yeast cells in culture systems. *Saccharomyces cerevisiae, Saccharomyces carlsbergensis*, and *Pichia pastoris* are the most commonly used yeast hosts, and are convenient fungal hosts. Control sequences for yeast vectors are known in the art. Mammalian cell lines available as hosts for expression are known in the art and include many immortalized cell lines available from the American Type Culture Collection (ATCC), such as CHO cells, and COS cells to name a few. Suitable promoters are also known in the art and include viral promoters such as that from SV40, Rous sarcoma virus (RSV), adenovirus (ADV), bovine papilloma virus (BPV), and cytomegalovirus (CMV). Mammalian cells may also require terminator sequences and poly A addition sequences; enhancer sequences which increase expression may also be included, and sequences which cause amplification of the gene may also be desirable. These sequences are known in the art. The transformed or transfected host cells can be used as a source of DNA sequences described above. When the recombinant molecule takes the form of an expression system, the transformed or transfected cells can be used as a source of the protein described below.

In another embodiment, the present invention relates to a Sequestrin protein having an amino acid sequence corresponding to SEQ ID NO: 2 and encompassing 652 amino acids or any allelic variation thereof. The amino acid sequence contains several tandem and nontandem degenerate peptide repeats. The cDNA clone of Sequestrin showed no homology with the *P. falciparum* variant antigen, PfEMP1, nor with the human erythrocyte anion transporter 3.

A polypeptide or amino acid sequence derived from the amino acid sequence in SEQ ID NO:2, refers to a polypeptide having an amino acid sequence identical to that of a polypeptide encoded in the sequence, or a portion thereof wherein the portion consists of at least 2–5 amino acids, and more preferably at least 8–10 amino acids, and even more preferably at least 11–15 amino acids, or which is immunologically identifiable with a polypeptide encoded in the sequence.

A recombinant or derived polypeptide is not necessarily translated from a designated nucleic acid sequence, or the sequence in SEQ ID NO: 1; it may be generated in any manner, including for example, chemical synthesis, or expression of a recombinant expression system. In addition the polypeptide can be fused to other proteins or polypeptides which increase its antigenicity, such as adjuvants for example. As an example, the protein (or polypeptide) can have an amino acid sequence corresponding to an epitope such as the CD36-binding domain defined above specified in SEQ ID NO: 4, or a portion thereof such as C-1 (1–12), C-2 (7–18), C-3 (13–25), C-4 (19–30), C-5 (25–36), C-6 (31–42), C-7 (37–48), C-8 (43–54), C9 (49–60), C-10 (55–68),C-11 (61–74), C-12 (67–78), C-13 (73–84), C-14 (79–90), C-15 (95–96), C-16 (91–102), C-17 (97–108), C-18 (103–114), C-19 (109–121), C-20 (115–126), C-21 (121–132), C-22 (127–138), and S-19 (39–54). In addition, the protein or polypeptide can be fused to other proteins or polypeptides which increase its antigenicity, thereby producing higher titers of neutralizing antibody when used as a vaccine. Examples of such proteins or polypeptides include any adjuvants or carriers safe for human use, such as aluminum hydroxide.

In a further embodiment, the present invention relates to a method of producing the recombinant or fusion protein which includes culturing the above-described host cells, under conditions such that the DNA fragment is expressed and the recombinant or fusion protein is produced thereby. The recombinant or fusion protein can then be isolated using methodology well known in the art. The recombinant or fusion protein can be used as a vaccine for immunity against infection with *P. falciparum* or as a diagnostic tool for detection of malaria infection. The transformed host cells can be used to analyze the effectiveness of drugs and agents which inhibit Sequestrin function, such as host proteins or chemically derived agents or other proteins which may interact with the parasite to down-regulate or alter the expression of Sequestrin or CD36 or affect the ability of Sequestrin-CD36 binding. A method for testing the effectiveness of an anti-malaria or anti-sequestration drug or agent can for example be the IRBC adhesion assay described below in the EXAMPLES, or micortiter assays, either by coating a surface with CD36 and measuring the binding of Sequestrin in the presence or absence of the drug or agent, or by coating with Sequestrin and measuring the binding of CD36 in the presence or absence of the drug or agent.

In another embodiment, the present invention relates to antibodies specific for the above-described recombinant proteins (or polypeptides). For instance, an antibody can be raised against a peptide having the amino acid sequence of SEQ ID NO: 2, or against a portion thereof of at least 10 amino acids, perferrably, 11–15 amino acids, or against the CD36-binding domain or SEQ ID NO: 4. Persons with ordinary skill in the art using standard methodology can raise monoclonal and polyclonal antibodies to the protein (or polypeptide) of the present invention, or a unique portion thereof. Material and methods for producing antibodies are well known in the art (see for example Goding, in, *Monoclonal Antibodies: Principles and Practice*, Chapter 4, 1986).

In a further embodiment, the present invention relates to a method of detecting the presence of malaria or antibodies against malaria in a sample. Using standard methodology well known in the art, a diagnostic assay can be constructed by coating on a surface (i.e. a solid support) for example, a microtitration plate or a membrane (e.g. nitrocellulose membrane), all or a unique portion of the Sequestrin protein described above, and contacting it with the serum of a person suspected of having malaria. The presence of a resulting complex formed between Sequestrin and antibodies specific therefor in the serum can be detected by any of the known methods common in the art, such as fluorescent antibody spectroscopy or colorimetry. This method of detection can be used, for example, for the diagnosis of malaria and determining the degree to which an individual is protected from infection or disease.

The adhesion properties of the *falciparum* parasite are critical to its survival and central to the development of pathology. Consequently, the ability of an individual to reduce parasite adhesion would determine the patient's ability to prevent infection or disease. This may take the form of antibodies which inhibit binding of Sequestrin to CD36; this can be measured in a microtiter assay for the detection of antibodies as described above or an assay for the detection of Sequestrin as described below. Such assays can be used to screen individuals after receiving a malaria vaccine to measure the production of protective antibodies. Another mechanism to reduce adhesion of Sequestrin to CD36 is by down-regulating or altering the adhesion receptors present on the endothelium. Sequestrin can be used to measure the availability of endothelium receptors by contacting labeled Sequestrin to target tissue either ex vivo or in vivo and measuring the degree to which labeled Sequestrin binds to target tissue. Sequestrin can be labeled by any detectable label known in the art such as a radionuclide, for example.

In yet another embodiment, the present invention relates to a method of detecting the presence of Sequestrin in a sample. Using standard methodology well known in the art, a diagnostic assay can be constructed by coating on a surface (i.e. a solid support) for example, a microtitration plate or a membrane (e.g. nitrocellulose membrane), antibodies specific for Sequestrin, and contacting it with serum or tissue sample of a person suspected of having malaria. The presence of a resulting complex formed between Sequestrin in the serum and antibodies specific therefor can be detected by any of the known methods common in the art, such as fluorescent antibody spectroscopy or colorimetry. This method of detection can be used, for example, for the diagnosis of malaria and for predicting the consequences of malaria. The amount of Sequestrin expressed may affect survival, multiplication, and therefore, degree of pathology (severe disease is generally associated, but not always, with higher levels of parasitemia). Binding to CD36 is a survival mechanism for parasites, and higher levels of Sequestrin expression may enhance parasite survival and therefore pathology. In addition, because a plethora of symptoms may result from *P. falciparum* infection, and binding to CD36 is known to involve several molecules, the expression of Sequestrin and other parasite adhesion counter receptors may either determine or reflect the pathology which can be expected from a particular isolate. Therefore, determining expression of Sequestrin in a sample from an infected patient may be used to predict the clinical consequences of the infection.

In another embodiment, the present invention relates to a diagnostic kit which contains the Sequestrin protein and ancillary reagents that are well known in the art and that are suitable for use in detecting the presence of antibodies to Sequestrin in serum or a tissue sample, specifically antibodies to *P. falciparum*. Tissue samples contemplated can be monkey and human, or other mammals.

In another embodiment, the present invention relates to a vaccine for protection against malaria. The vaccine comprises Sequestrin protein or a portion thereof, for example the CD36-binding domain which could elicit antisequestration antibodies. The vaccine can be prepared by inducing expression of the recombinant expression vector described above in either a prokaryotic or eukaryotic host and purifying the recombinant or fusion protein described above. The purified solution is prepared for administration to mammals by methods known in the art, which can include filtering to sterilize the solution, diluting the solution, adding an adjuvant and stabilizing the solution. The vaccine can be lyophilized to produce a malaria vaccine in a dried form for ease in transportation and storage. Further, the vaccine may be prepared in the form of a mixed vaccine which contains the recombinant protein described above and at least one other antigen as long as the added antigen does not interfere with the effectiveness of the malaria vaccine and the side effects and adverse reactions are not increased additively or synergistically.

The vaccine may be stored in a sealed vial, ampule or the like. The present vaccine can generally be administered in the form of a liquid or suspension, In the case where the vaccine is in a dried form, the vaccine is dissolved or suspended in sterilized distilled water before administration. Generally, the vaccine may be administered orally, subcutaneously, intradermally or intramuscularly in a dose effective for the production of neutralizing antibody and protection from infection or disease.

In yet a further embodiment, the present invention relates to DNA or nucleotide sequences for use in detecting the presence or absence of Sequestrin using the polymerase chain reaction (PCR). The DNA sequence of the present invention can be used to design primers which specifically bind to Sequestrin cDNA for the purpose of detecting the presence, absence, or quantitating the expression of Sequestrin. The primers can be any length ranging from 7–40 nucleotides, preferably 10–15 nucleotides, most preferably 18–25 nucleotides. Reverse transcription reactions for converting mRNA into cDNA and reagents and controls necessary for PCR reactions are well known in the art. The amplified products can then be analyzed for the presence or absence of Sequestrin sequences, for example by gel fractionation, with or without hyridization, by radiochemistry, and immunochemical techniques.

In another embodiment, the present invention can be used to diagnose *P. falciparum* malaria by detecting the presence or absence of Sequestrin in genomic DNA, using PCR or other techniques well known in the art. All *P. falciparum* isolates tested thus far appear to have Sequestrin in their genome.

In yet another embodiment, the present invention relates to a diagnostic kit which contains PCR primers specific for Sequestrin, and ancillary reagents that are well known in the art and that are suitable for use in detecting the presence or absence of Sequestrin in a sample using PCR. Samples contemplated can be human or other mammals.

In another embodiment, the present invention relates to a DNA-based vaccine. The Sequestrin DNA fragment of the present invention described in SEQ ID NO: 1 or a portion thereof, or an allelic form thereof, can be administered as a DNA-based vaccine to protect against malaria. The Sequestrin DNA vaccine can be injected alone, or combined with at least one other antigen or DNA fragment as long as the added antigen or DNA fragment does not interfere with the effectiveness of the malaria vaccine and the side effects and adverse reactions are not increased additively or synergistically.

The DNA-based vaccine of the present invention can be administered for example intermuscularly, or alternatively, can be used in nose drops. The DNA fragment or a portion thereof can be injected as DNA, as DNA encapsulated in liposomes, as DNA entrapped in proteoliposomes containing viral envelope receptor proteins (Nicolau, C. et al. *Proc. Natl. Acad. Sci. U.S.A.* 1983, 80, 1068; Kanoda, Y., et al. *Science* 1989, 243, 375; Mannino, R. J. et al. *Biotechniques* 1988, 6, 682). Alternatively, the DNA can be injected along with a carrier. A carrier can be a protein or such as a cytokine, for example interleukin 2, or a polylysine-glycoprotein carrier (Wu, G. Y. and Wu, C. H. J. *Biol. Chem.* 1988, 263,14621), or a nonreplicating vector, for example expression vectors containing either the Rous sarcoma virus or cytomegalovirus promoters. Such carrier proteins and vectors and methods for using same are known to a person in the art (See for example, Acsadi, G. et al. *Nature* 1991, 352, 815–818). In addition, the DNA could be coated onto tiny gold beads and said beads introduced into the skin with, for example, a gene gun (Cohen, J. *Science* 1993, 259, 1691–1692; Ulmer, J. B. et al. *Science* 1993, 259, 1745–1749). The DNA fragment can further be administered in a bacterial vector such as Shigella or Salmonella.

In another embodiment, the present invention relates to a method of reducing malaria disease symptoms in a patient by administering to said patient an effective amount of Sequestrin DNA, antisense RNA, anti-Sequestrin antibodies as described above, Sequestrin protein or analogs thereof, or agents capable of blocking Sequestrin function or expression. Blocking Sequestrin is shown to inhibit or reverse the adhesion of infected red blood cells to CD36, a receptor on the endothelial wall, thereby inhibiting both the sequestration of IRBC and the development of severe malaria. The Sequestrin DNA or antisense RNA of the present invention described in SEQ ID NO: 1 can be used to design degenerate oligonucleotides which can be administered to a patient for the purpose of blocking Sequestrin function thereby preventing the development of cerebral malaria in the patient or reducing malaria disease symptoms.

The DNA-based vaccine can be injected alone, or combined with a least one other antigen or DNA fragment as long as the added antigen or DNA fragment does not interfere with the effectiveness of the Sequestrin DNA or antisense RNA and the side effects and adverse reactions, if any, are not increased additively or synergistically. The DNA can be converted to antisense RNA for example by subcloning the said DNA into a transcriptional vector, such as pGEM family of plasmid vectors, or under control of a transcriptional promoter of a virus such as vaccinia, and the RNA used as naked RNA for hybridization with the sense RNA, inhibiting the production of Sequestrin by inhibiting the translation of the sense RNA.

When providing a patient with Sequestrin DNA, antisense RNA, anti-Sequestrin antibodies, Sequestrin or analogs thereof, or agents capable of inhibiting Sequestrin function or expression to a recipient patient, the dosage of administered agent will vary depending upon such factors as the patient's age, weight, height, sex, general medical condition, previous medical history, etc. In general, it is desirable to provide the recipient with a dosage of the above compounds which is in the range of from about 1pg/kg to 10 mg/kg (body weight of patient), although a lower or higher dosage may be administered.

Described below are examples of the present invention which are provided only for illustrative purposes, and not to limit the scope of the present invention. In light of the present disclosure, numerous embodiments within the scope of the claims will be apparent to those of ordinary skill in the art.

The following MATERIALS AND METHODS were used in the examples that follow.

Proteins and Antibodies

CD36, a kind gift from Dr. N. Tandon, American Red Cross, Rockville Md. was prepared as described (Tandon et al. (1989) *J. Biol. Chem.* 264: 7570–7575). CD36 (10 ug) was radiolabeled with NaI (1 mCi to a specific activity of 7 33 $10^7$ cpm/mg by Iodobeads (Pierce, Rockford, Ill.). Immunoaffinity-purified CD36 from C32 melanoma cells was prepared as essentially described by Barnwell et al. (1989) except that anti-CD36 monoclonal antibody MO52 was used as the immunoabsorbent. Peptides were synthesized on an Applied Biosystems 430A peptide Synthesizer (Foster City, Calif.) and were >90% pure by HPLC. The peptides were derived from three regions of the deduced amino acid sequence from cDNA clone 2A1-B3 and are designated as: i) S-19, DEFEHKILLEELNKMDKDEL (SEQ ID NO: 5); ii) P-17, NLELEEIDRLYKEELD (SEQ ID NO: 6); iii) P-YL, YLEELEKIDKEEKEKI (SEQ ID NO: 7).

Monoclonal antibodies (Mab) OKM8 and OKM5 were obtained from Dr. P. Rao (Ortho Pharamceutical Corp, Raritan, N.J.). Rabbit OKM8 anti-idiotype antibodies were prepared as described (Ockenhouse et al., 1991, supra). IgG fractions from the pre-immune sera was prepared by affinity chromatography on protein A-Sepharose. IgG fractions from a Mab OKM8-immunized rabbit was prepared by affinity chromatography on a OKM8-Speharose affinity column.

Purified Sequestrin recombinant protein GST-R(0–I) or synthetic peptides conjugated to keyhole limpet hemocyanin (KLH) were emulsified in Freund's complete adjuvant (FCA) and Freund's incomplete adjuvant (FIA). Polyclonal anti-Sequestrin antibodies were produced in BALBIc mice by 4 intraperitoneal injections and in NZW rabbits by 4 intramuscular injections every three weeks (100 µg/immunization). The initial immunization was administered in FCA followed by 3 booster immunizations in FIA.

Expression Cloning

A *P. falciparum* (strains ItG, NF54, and clone 3D7) trophozoite/schizont stage cDNA library constructed using EcoRI/NotI linkers in λgt11 bacteriophage (kind gift of Dr. Luther Lindler, WRAIR) was plated on *E. coli* strain Y 1090, and filter immobilized plaques were probed with $^{125}$I-CD36 diluted to 106 cpm/ml in 10 mM TrisHCl (pH 8.0)/150 mM NaCl/0.05 Tween 20 (TNT buffer) overnight at 4° C., then washed three times for 10 minutes in TNT with 0.1 bovine serum albumin (BSA) with 0.2% NP40. Autoradiography at 4° C. for 6–72 hours was performed to identify positive colonies. Bacteriophage DNA was purified from a plate lysate of clone 2A1-B3, the insert removed by digestion with EcoRI and inserted into pUC13 (Pharmacia Biotech, Inc. Piscataway, N.J.), and the complete insert nucleotide sequence from both strands of clone p13-36B determined by the dideoxynucleotide terminator method.

Recombinant Protein Expression

β-galactosidase fusion proteins were prepared with recombinant λgt11 bacteriophage clone 2A 1-B3 which was lysogenized in *E. coli* strain Y 1089. Clones were grown in LB medium and protein expression induced in the presence of 10 mM isopropylthio-β-D-galactoside (IPTG). To create recombinants for production of trpE (define what are trp E inserts, vector obtained from where) fusion proteins, DNA inserts were amplified by polymerase chain reaction (PCR) from clone p13-36B using primers with appropriate restriction sites, digested with BamHI and HindIII, then ligated into vector pATH2 (a gift from D. Kaslow, NIH). After electroporation into *E. coli* strain DH10B, selected clones were grown to density in LB medium with 100 mg/ml ampicillin, then diluted 1:100 in M9 salts (Gibco/BRL, Gaithersburg, Md.)/0.002% thiamine/1 mM $MgSO_4$/0.1 mM $CaCl_2$/0.25 glucose/1% casamino acids/100 mg/ml ampicillin. After 6 h growth, indoeacrylic acid was added to 10 mg/ml, and bacteria allowed to grow to saturation.

A glutathione S-transferase expression vector was constructed by cloning DNA inserts amplified by polymerase chain reaction (PCR) from *P. falciparum* (strain ItG) genomic DNA using primers with 5' BamHI and 3' ECoRI restriction restriction sites. PCR products were restriction enzyme digested and ligated into vector pGEX-3X (Pharmacia Biotech, Inc. Piscataway, N.J.). Alternatively, partially overlapping, complementary synthetic oligonucleotides were annealed, blunt-ended with T7 DNA polymerase (US Biochemical, Cleveland, Ohio), then digested with BamHI and EcoRI and ligated into pGEX-3X. After electroporation into *E. coli* strain DH10B, selected clones were grown overnight at 37° C. in Super Broth with 100 ug/ml ampicillin, then diluted 1:10 and grown for 2–3 hours, and finally allowed to grown for 2–6 hours in the presence of 0.1 mM IPTG. Cells were disrupted by sonication in ice-cold PBS and insoluble particulate matter removed by centrifugation. Soluble GST fusion proteins were purified on glutathione resin (Glutathione Sepharose 4B; Pharmacia Biotech, Inc. Piscataway, N.J.), eluted in 10 mM reduced glutathione/50 mM TrisHCl, pH 8.0, and dialyzed against PBS. In some experiments, recombinant Sequestrin GST-fusion proteins were cleaved from the GST fusion partner by enzymatic digestion with Factor Xa according to the manufacturer's recommendations (Pharmacia Biotech, Inc. Piscataway, N.J.) and purified proteins dialyzed extensively against PBS.

Sequestrin-CD36 Binding Assays

Recombinant λgt11 bacteriophage clone 2A1-B3 or control bacteriphage clone 2211 F expressed as β-galactosidase fusion proteins were electrophoresed on SDS-PAGE, transferred to nitrocellulose and probed with 1×10$^7$ cpm of $^{125}$I-CD36 diluted in TNT overnight at 4° C. After extensive washing, autoradiography was performed to confirm the specificity of binding of CD36 to the Sequestrin insert.

Assays to detect CD36 binding to immobilized Sequestrin fusion proteins were performed as follows: GST fusion proteins or control proteins were diluted in PBS and allowed to adsorb to 96-well microtiter plates overnight at 4° C. Non-specific binding sites were saturated with 0.5% BSA in 1% Tween 20 for 2 hours at room temperature. $^{125}$I-CD36 (100,000 cpm per well) diluted in Tris-buffered saline (TBS) pH 7.5/0.1% Tween 20 (TBS-T) were added for 1 hour. Wells were subsequently washed with TBS-T, and radioactivity measured by automatic gamma counter (ClinGamma 1272, LKB Wallac, Finland). In some experiments, increasing concentrations of unlabeled CD36 was added to competitively inhibit binding of $^{125}$I-labeled CD36 to GST-R (0–IV). IC50 values were determined by extrapolating the linear portion of the inhibition curve to determine the 100% inhibition value.

Studies to measure Sequestrin fusion protein binding to immobilized CD36 were performed using an enzyme-linked assay. CD36 (0.3 µg/ml in PBS) was coated overnight into 96-well microtiter plates. After blocking non-specific sites with 0.5% BSA/1% Tween 20, biotinylated GST-R(0–I) (Biotinylation kit; Amersham Inc., Arlington Heights, Ill.) was diluted to 0.5 µg/ml in TBS-T and added to the microtiterplates for 2 hours at 37° C. Wells were washed three times and alkaline phosphatase-conjugated streptavidin (Gibco-BRL Life Technologies, Gaithersburg, Md.) was added to wells for 1 hour. After washing, calorimetric changes in the substrate p-nitrophenylphoshate (PNPP) were measured kinetically at 405 nm absorbance by microplate reader (EL 312e; Bio-Tek Instruments Inc., Winooski, Vt.). In some experiments, anti-CD36 monoclonal antibodies were pre-incubated for 1 hour in wells coated with CD36 prior to the addition of biotinylated GST-R(0–I). To assay inhibition by CD36 anti-idiotype antibodies, biotinylated GST-R(0–I) was preincubated with various concentrations of purified rabbit OKM8 anti-idiotype antibodies prior to the addition to CD36-coated microtiter plates.

Parasite Culture and IRBC Adhesion Assays

P. falciparum parasite strains ItG-2F6, the 3D7 clone of NF54, and Aotus monkey-derived MC K$^+$C$^+$ parasites (phenotypically knob and cytoadherent positive) were adapted to continuous culture in human erythrocytes. Parasitized erythrocytes were enriched for mature trophozoite and schizont stages by gelatin flotation. In some experiments ItG-ICAM parasites selected for increased adhesion to both CD36 and ICAM-1 were used. MC K$^-$C$^-$ parasites (phenotypically knob negative and cytoadherent deficient) were selected for increased binding to CD36 as described (Ockenhouse et al., 1991, supra).

IRBC binding to CD36-coated or ICAM-1 coated surfaces was performed as described (Ockenhouse et al., 1991, supra). Briefly, CD36 (0.5 µg/ml) or control proteins were coated ovrnight at 4° C. onto polystyrene petri dishes and non-specific sites blocked with 1% BSA in PBS. GST fusion proteins were added for 45 minutes and aspirated prior to the addition of malaria-infected erythrocytes (6×10$^6$/ml). After 45 minutes incubation at room temperature, the non-adherent erythrocytes were removed by washing, and the adherent erythrocytes fixed in 1% glutaraldehyde, stained with Giemsa stain, and the number of IRBC bound per mm$^2$ surface area quantitated by light microscopy. In some experiments, IRBC were pre-incubated with various dilutions of heat-inactivated preimmune or immune rabbit anti-Sequestrin antiserum for 1 hour at 37° C.

IRBC binding assays to C32 melanoma cells were performed as described (Ockenhouse et al., 1991, supra). To measure the effect recombinant proteins have on blocking IRBC binding to C32 cells, fusion proteins (20 µg/ml) were incubated with C32 melanoma cells for 45 minutes prior to the addition of IRBC (1×106 IRBC/well in RPMI 1640 medium). After 45 minutes incubation, non-adherent erythrocytes were removed by washing and cells processed as described above. To measure the effect recombinant proteins have on reversing the adhesion of IRBC bound to C32 cells, IRBC (2×106 IRBC/well in RPMI 1640 medium) were pre-incubated with C32 cells for 1 hour and non-adherent erythrocytes removed by washing the plates three times with RPMI 1640. GST fusion proteins (20 µg/ml) were added and the plates were rotated on a rocking platform at 50 cycles per minute for 1 hour at 37° C. IRBC displaced by GST fusion proteins were removed by washing three times with RPMI 1640 and the remaining bound IRBC were fixed, stained, and quantitated as the number of IRBC bound per 100 melanma cells. All in vitro assays were carried out with the ItG-2F6 clone of P. falciparum and results of binding inhibition validated with P. falciparum parasites from the 3D7 clone of NF54.

Immunoprecipitation and Immunoblotting

Synchronized IRBC were concentrated by Percoll density gradient centrifugation or gelatin sedimentation and sequentially extracted with 1% Triton X-100 in PBS followed by extraction of the Triton X-100 insoluble portion with 2% SDS in PBS supplemented with leupeptin (10 µg/ml) to a final concentration of 2.5×10$^8$ parasite/ml. For immunoblotting, 2.5×10$^6$ parasite equivalents were electrophoresed in 5% SDS-PAGE gels, transferred to nitrocellulose and blocked for 1 hour in 10% non-fat dry milk in PBS. Polyclonal antibodies diluted in TBS-T were added for 1 hour and the membranes were washed 3 times for 5 minutes each in TBS-T. Secondary antibodies 1:10000 (Amersham, Arlington Heights, Ill.) labeled with horse-radish peroxidase (HRPO) were incubated with membranes for 1 hour followed by extensive washing and detection of specific protein bands by enhanced chemiluminescence (ECL; Amersham, Arlington Heights, Ill.).

The detection of Sequestrin on the surface of the erythrocyte was assessed by surface biotinylation of IRBC by incubation with 1 mM sulfo-NHS-biotin in PBS (Pierce, Inc. Rockford, Ill.) for 5 minutes at room temperature. IRBC were washed 2 times in PBS and sequentially extracted with Triton X-100 and SDS as described above. Aliquots (1×10$^7$ parasites) of the SDS-extracted were diluted 20 fold in 1% Triton X-100/PBS and immunoprecipitated with polyclonal anti-GST-R(0–I) antibody. Immunoprecipitates were complexed with Protein A-Sepharose, washed, run on 5% SDS-polyacrylamide gels, and transferred to nitrocellulose membrane. Surface-labeled proteins were detected by incubation of membranes with streptavidin-HRPO followed by ECL.

Immunofluorescence

Surface immunofluorecence of IRBC (ItG-2F6 clone) with rabbit-anti-GST-R(0–I) polyclonal antibody was performed as previously described (Ockenhouse et al., 1991, supra) except that IRBC were sequentially incubated with primary rabbit antisera, goat anti-rabbit IgG, and FITC-labeled sheep anti-goat IgG. Covalently coupling of GST-R(0–I) fusion protein to 0.54 mm fluorececent latex microspheres (Covaspheres, Duke Scientific, Palo Alto, Calif.) was carried out as recommended by the manufacturer. Microspheres (x xx 10x/ml in RPMI 1640) were added to C32 melanoma cells for 30 minutes. After extensive washing of non-bound fluorescent micropspheres, cells were fixed in 1% glutaraldehyd/PBS and photographed under UV light.

ELISA

Capture proteins were diluted to 0.3 mg/ml and coated overnight at 4° C. onto Immulon 2 microtiter plates. Plates were blocked in 0.5% BSA in Tris-buffered saline (TBS) plus 1% Tween 20 for 1 hour. Rabbit anti-idiotype IgG or preimmune IgG were added for 1 hour followed by three washes in TBS-T. Biotinylated GST-R(0–I) (0.5 mg/ml) was added for 1 hour. After three washes in TBS-T alkaline phosphatase-conjugated streptavidin (Gibco-BRL Life Technologies, Gaithersburg, Md.) was added for 1 hour. Colorimetric changes in the substrate p-nitrophenylphoshate (PNPP) were measured kinetically at 405 nm absorbance and are shown as m OD units per minute.

EXAMPLE 1

Identification of Sequestrin by Expression Cloning

A cDNA expression library from *P. falciparum* parasite strains ItG, NF54, and NF54 clone, 3D7 was constructed in λgt11 bacteriophage with approximately 80% of the clones containing inserts. The library which was plated on *E. coli* strain Y 1090 and induced to express β-galactosidase fusion proteins was probed with $^{125}$I-radiolabeled CD36. A single plaque (λ2A1) out of 60,000 cloned inserts was identified which bound ligand on duplicate filters. After 2 plaque purifications, >95% of plaques supported binding of CD36, and a single clone (λ2A1-B3) was selected for further analysis.

The binding of CD36 to protein expressed by phage λ2A1-B3 was highly specific. When clone λ2A 1-B3 was plated to confluence on bacteria, induced to express fusion protein, and the filter-immobilized plaques screened with $^{125}$I-CD36, nearly 100% of clones bound CD36. A control phage, randomly isolated from the cDNA library, was plated in similar manner but demonstrated no binding of CD36. λ2A1-B3 was lysogenized in *E. coli* strain Y 1089, permitting large scale production of the fusion protein. A control lysogenized clone, λ2211F (a gift of S. Cohen, WRAIR), had been isolated from the same cDNA library by monoclonal antibody FC2 which reacts to the surface of the Mayer's cleft in *P. falciparum* parasites. Immunoaffinity-purified fusion protein obtained from both clones was separated by SDS-PAGE, transferred to nitrocellulose, and immunoblotted with anti-β-galactosidase antisera which recognized a fusion protein of approximately 170 kD. Monoclonal antibody FC2 recognized the fusion protein expressed by λ2211F, but demonstrated no reactivity with protein expressed by λ2A1-B3; conversely, radiolabelled CD36 bound strongly to protein expressed by λ2A1-B3, but not at all with λ2211F-expressed protein (FIG. 1).

The 2 kB insert from purified λ2A1-B3 DNA was removed by digestion with endonuclease EcoRI, and inserted into vector pUC13. Clone p13-36B was selected by blue/white screening on X-galactoside, and both strands of the insert sequenced with synthetic oligonucleotides by the dideoxynucleotide chain termination method (Sanger et al. (1977) *Proc. Natl. Acad. Sci. U.S.A.* 74:5463–5467). The sequenced gene fragment encoding 1958 nucleotides of open reading frame (SEQ ID NO: 1) is A-T rich (A, 53%; T, 23%), a feature characteristic of other genes of malaria parasite origin. The deduced amino acid sequence of 652 amino acids (SEQ ID NO:2) contained several tandem and nontandem degenerate peptide repeats. The tandem repeats included 3 repeats of an asparagine/threonine-rich decamer (residues 9–38) and 14 repeats of a hexamer (residues 542–625) rich in asparagine and aspartate. Between amino acid residues 63 and 362, paired glutamates (E—E) appeared 14 times. The E—E pair typically appeared as part of a nontandemly repeated 14 amino acid motif with homology to annexins type I and II in amino acids N354–E359. The cDNA clone of Sequestrin revealed no homology with the *P. falciparum* variant antigen, PfEMP1, nor with the human erythrocyte anion transporter band 3.

In order to define which parasite strain was represented in clone p13-36B, genomic DNA from ItG and 3D7 *P. falciparum* parasites was prepared and PCR products representing several distinct regions of clone p13-36B were sequenced. While a high degree of homology was observed between both ItG and 3D7 gDNA, several distinct nucleotide changes in the ItG sequence differed with the p13-36B sequence (results not shown). The deduced nucleotide sequence from 3D7 parasite gDNA matched the sequence from clone p13-36B.

EXAMPLE 2

Delineation of the CD36-binding Domain

In order to better define the CD36-binding site, overlapping fragments representing the entire 652 amino acids were expressed as trpE fusion proteins in *E. coli*. Bacterial extracts containing the fusion proteins were separated by SDS-PAGE, transferred to nitrocellulose, and probed with radiolabelled CD36. Fusion proteins representing amino acids E1-M60, A370-D542, and Q504-V652 failed to support binding while the fusion protein representing amino acids H42-A458, which contains the repeated E—E pairs as well as a carboxy-terminal asparagine rich domain, supported binding of radiolabelled human CD36 but not radiolabeled ICAM-1 (data not shown).

Figure 2A:
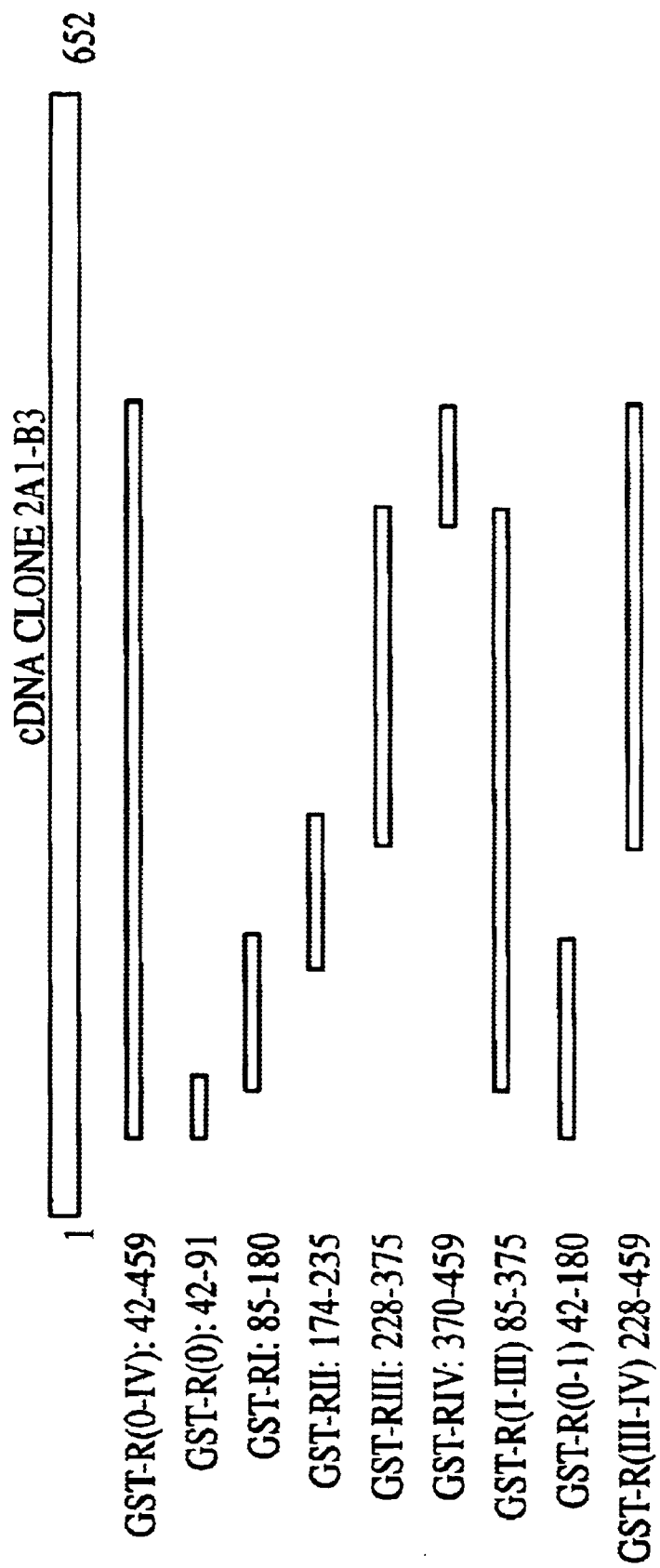
FIG. 2 shows (A) Schematic map of overlapping regions of Sequestrin clone 2A1-B3 expressed as GST fusion proteins (B) Coomasie blue stained gel of glutathione-Sepharose affinity-purified GST fusion proteins.
Figure 2B:
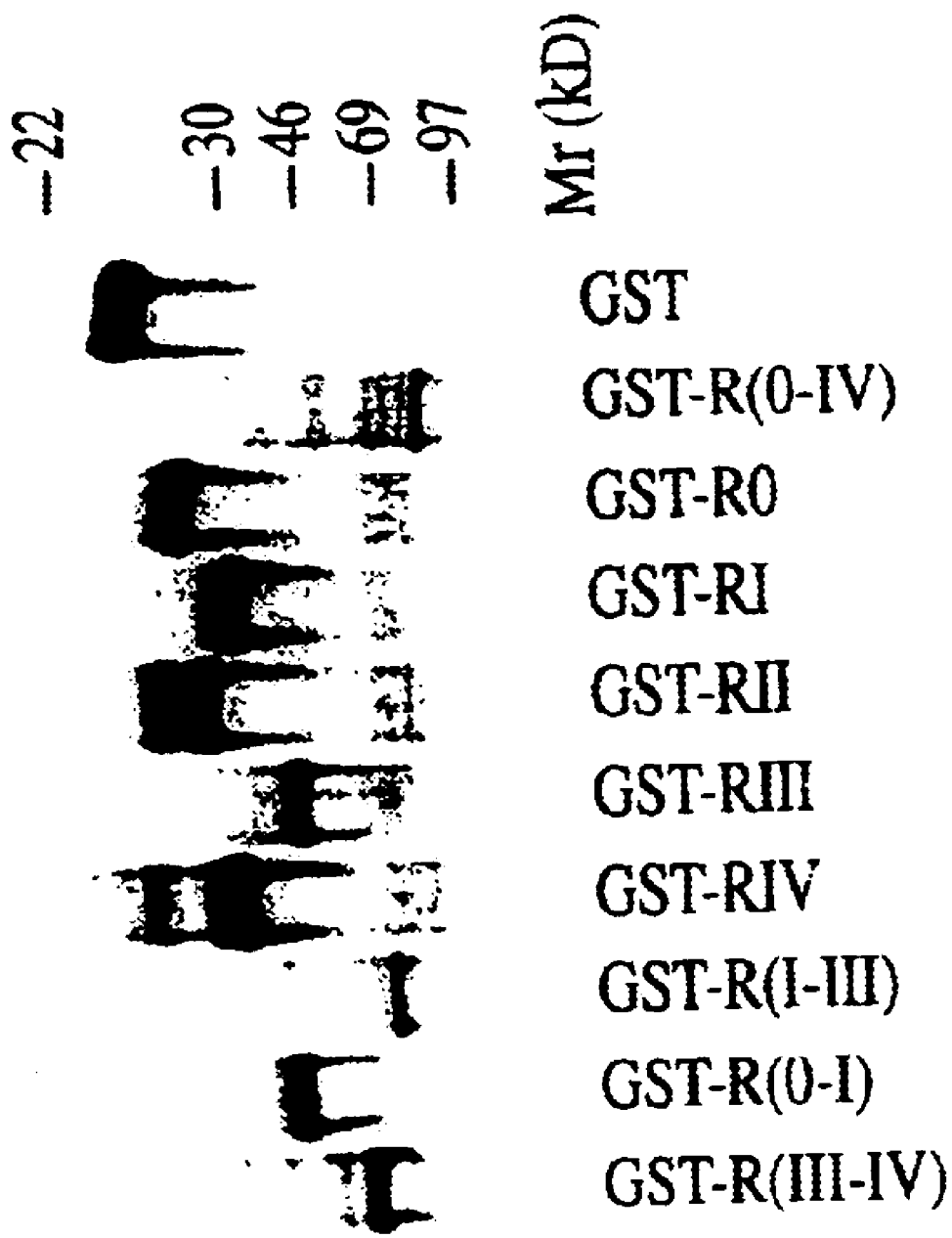
Figure 3B:
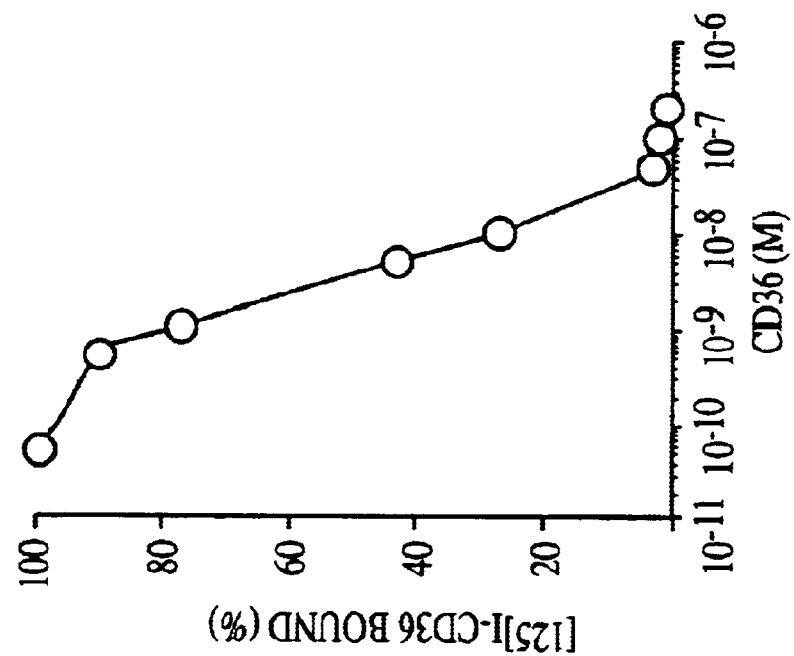
FIG. 3 demonstrates CD36 binding to Sequestrin-GST fusion proteins (A). GST fusion proteins were coated overnight onto microtiter plates and incubated with $^{125}$I-CD36 for 1 hr at room temperature. Mictotiter wells were washed and bound $^{125}$I-CD36 was detected by gamma counting. (B) Competitive inhibition of $^{125}$I-CD36 binding to Sequestrin GST R(0–IV) fusion protein by unlabeled CD36 revealed a Ki of ~6 nM.
Figure 3A:
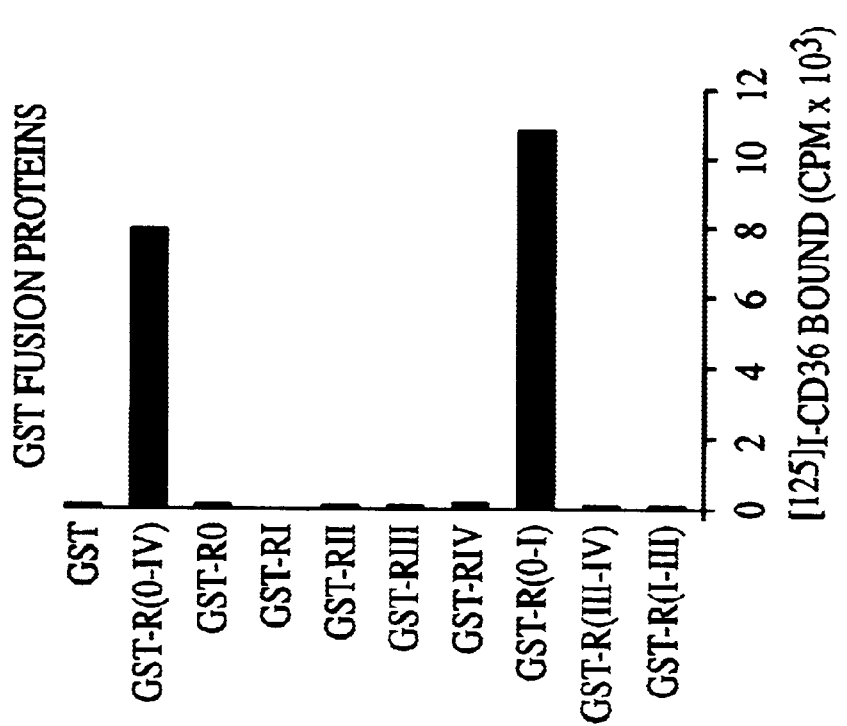

The CD36 binding domain within amino acids H42-A458 was further refined by the construction and expression of overlapping proteins fused to glutathione-S-transferase (GST). The Sequestrin protein fragment was divided into five domains (R0–RIV) with a 6–7 amino acid overlap representing individual domains (R0, RI, RII, RIII, RIV) or combinations of domains (R(I–III) and R(0–IV) (FIG. 2A). Fusion proteins were expressed, affinity-purified on glutathione-Sepharose and resolved by SDS-PAGE (FIG. 2B). After transfer to nitrocellulose, the fusion proteins were probed with $^{125}$I-CD36. CD36 binding was not detected in any of the individual domains, representing the entirety of amino acids H42-A458 nor was binding observed with domain combination R(I–III). Only domain combination R(0–IV) bound radiolabelled CD36 (results not shown). Similar results were obtained by coating equal concentrations of purified fusion protein or GST alone onto microtiter plates followed by incubation with $^{125}$I-CD36. None of the recombinant proteins demonstrated significant (>2 fold) increases in bound CD36 compared to GST alone except domain combination R(0–IV) (FIG. 3A). To further delineate the CD36-binding domain, truncated GST fusion proteins encompassing regions 0+I or III +IV were constructed and tested for $^{125}$I-CD36 binding. Only GST-R(0–I) supported binding to CD36. Specificity of binding of $^{125}$I-CD36 to GST-R(0–IV) was demonstrated by competition with unlabeled CD36 with a Ki of approximately 6 nM (FIG. 3B).

Figure 4:
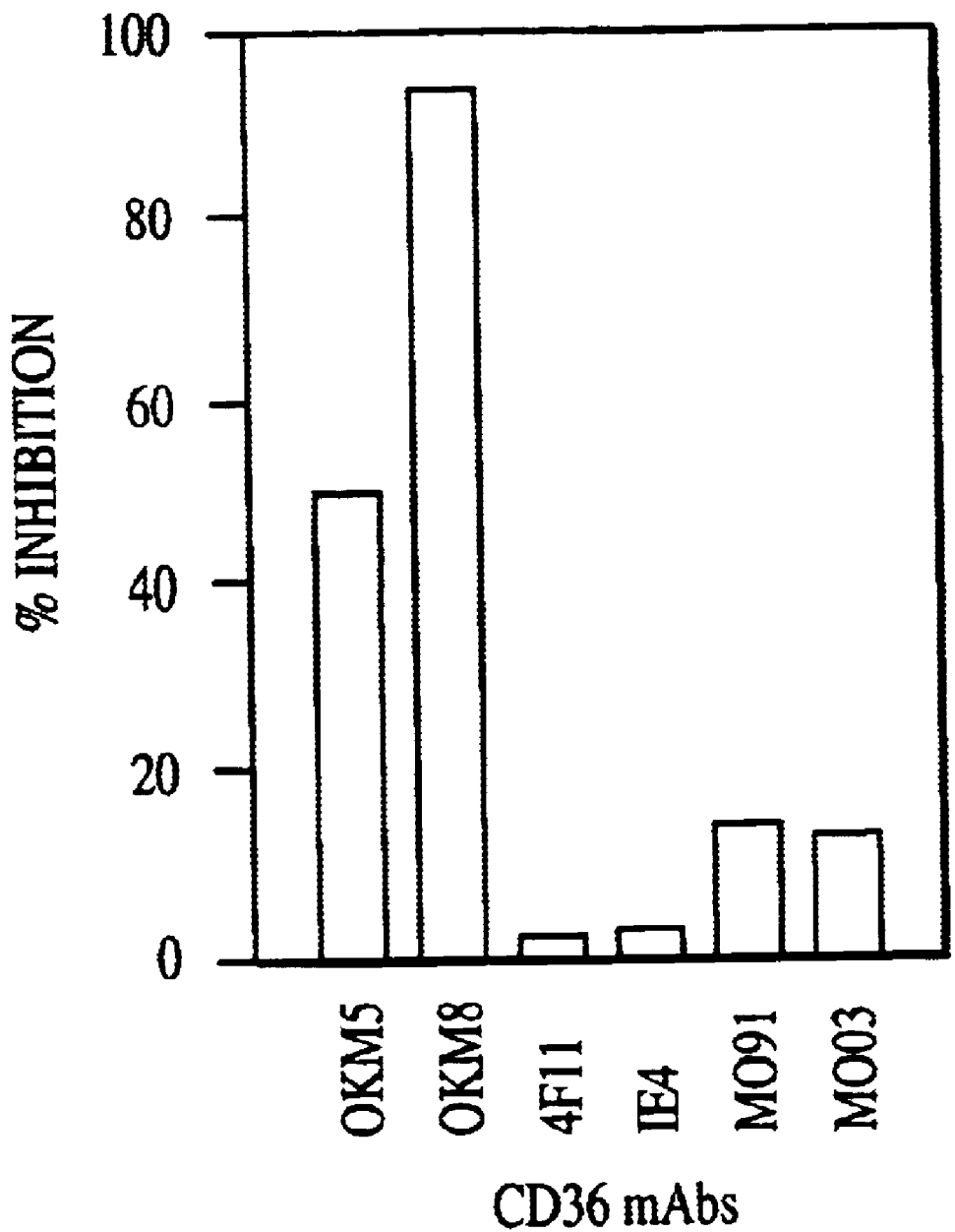
FIG. 4 shows that Sequestrin domain R(0–I) binds CD36 at an epitope defined by monoclonal antibodies OKM5/8. Microtiter wells coated with CD36 were preincubated for 1 hr at room temperature with several CD36-specific monoclonal antibodies recognizing distinct epitopes. After washing, biotinylated GST-R(0–I) was added for 2 hrs followed by a 1 hr incubation with strepavidin-alkaline phosphatase. Bound GST-R(0–I) was detected by measuring change in absorbance at 405 nm for 1 hour. Results are recorded as mean percent inhibtion of duplicate samples compared to control wells incubated in the absence of anti-CD36 monoclonal antibodies.

The CD36-Sequestrin interaction occured regardless of whether Sequestrin fusion proteins or CD36 was adsorbed onto a solid surface. Several CD36 epitopes defined by inhibitory monoclonal antibodies OKM5 and OKM8 have been implicated in IRBC adhesion to purified microvascular endothelium. Both Mabs OKM8 and OKM5 inhibited the binding of biotinylated GST-R(0–I) to purified CD36 while anti-CD36 Mabs which have no effect on IRBC-CD36 cytoadherence had no effect in the competitive ELISA assay (FIG. 4).

EXAMPLE 3

Sequestrin-CD36 Anti-idiotype Binding

Figure 5A:
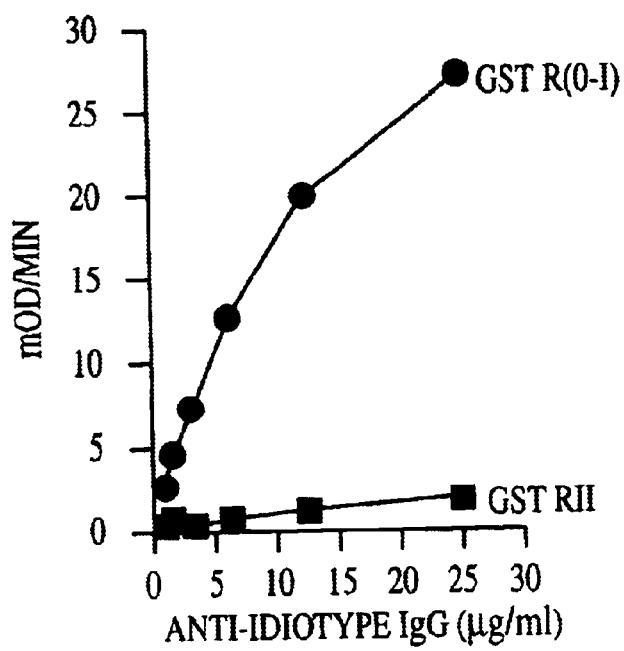
FIG. 5 shows CD36 anti-idiotype antibody binding to Sequestrin R(0–I). (A) Increasing concentrations of pre-immune or immune anti-idiotype IgG was incubated with microtiter plates coated with either GST-R(0–I) or GST-RII fusion proteins. Bound antibody was detected by absorbance readings at 405 nm every 2 minutes for 1 hr (B) Inhibition of binding of biotinylated GST-R(0–I) to CD36 by anti-idiotype antibodies. CD36-coated microtiter wells were incubated with biotinylated GST-R(0–I) in the presence of increasing concentrations of pre-immune or immune anti-idiotype IgG. Results are recorded as mean percent inhibtion of duplicate samples compared to control wells incubated in the absence of antibody.
Figure 5B:
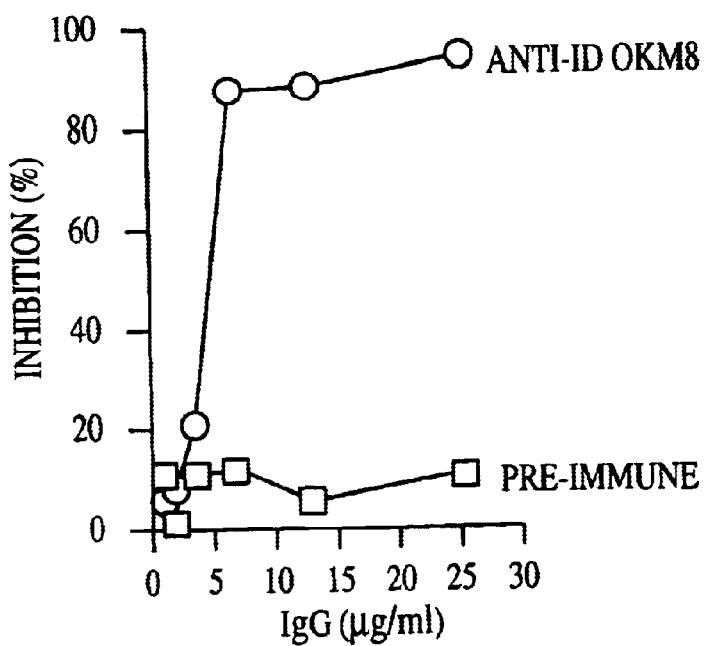

Sequestrin was originally defined as an IRBC surface protein of high molecular weight recognized by CD36 anti-idiotype antibodies (Ockenhouse et al., 1991, supra). Polyclonal anti-idiotype antisera were prepared by rabbit immunization with the inhibitory anti-CD36 Mab OKM8 to produce anti-idiotype antibodies mimicking the CD36 epitope for OKM8. Purified IgG fractions from both the pre-immune and immune sera were assayed for binding to Sequestrin fusion proteins by ELISA (FIG. 5). Only domain R(0–I) bound anti-idiotype antibodies while no detectable antibody binding occured to the adjacent RII domain (FIG. 5A). In addition, the anti-idiotype IgG competitively blocked binding of biotinylated GST-R(0–I) to CD36 (FIG. 5B) confirming the observation that Sequestrin recognition of both CD36 and its anti-idiotype mimic is identical.

EXAMPLE 4

Figure 6A:
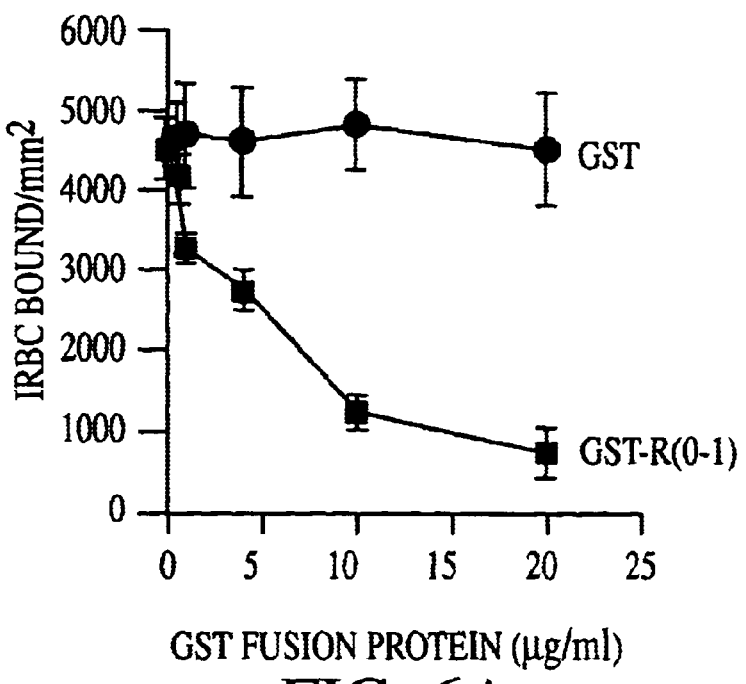
FIG. 6 shows the inhibition of binding of *P. falciparum* IRBC (ItG strain) to CD36 and C32 melanoma cells by the Sequestrin CD36-binding domain R(0–I). (A). Increasing concentrations of GST-R(0–I) fusion protein but not GST alone inhibit the binding of IRBC to CD36. Results are mean +s.d. of quadruplicate samples. (B) Inhibition and reversal of IRBC binding to C32 melanoma cells by factor Xa cleaved-R(0–I) and R(0–IV) but not RIII Sequestrin fragments. Results are indicated as mean percent inhibition of duplicate samples compared to control IRBC binding (inhibition assay, 950 IRBC bound/100 C32 cells; reversal assay, 778 IRBC bound/100 C32 cells)] in the absence of GST-fusion proteins.
Figure 6B:
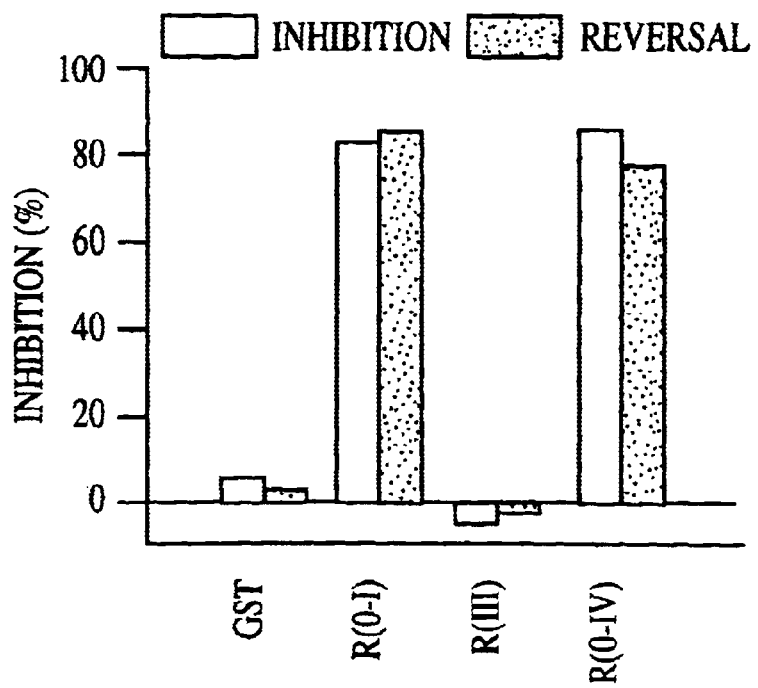
Figure 7:
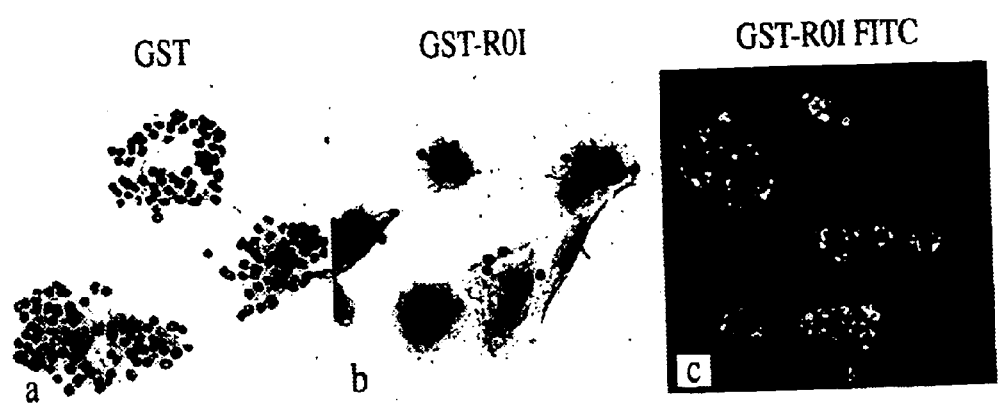
FIG. 7 demonstrates that the binding of Sequestrin GST-(R0–I) to C32 cells reverses cytoadherence of IRBC. IRBC were incubated with C32 cells for 1 hour and wells washed to remove non-adherent red cells. GST or GST-R(0–I) at 20 μg/ml was added and tissue culture plates rotated for 1 hour at 37° C. Displaced IRBC were removed and the cells were fixed and stained. A representative field indicating bound IRBC to C32 cells in the presence of GST (A) or GST-R (0–I) (B) is indicated. (C) Fluorescent microspheres covalently coupled to GST-R(0–I) fusion protein decorate the surface of CD36$^+$ C32 cells.

Inhibition of IRBC Binding by Sequestrin Fusion Proteins and anti-Sequestrin Antibodies Definitive proof that Sequestrin is a cytoadherence receptor for the CD36 endothelial counter-receptor must be validated by the demonstration of competitive inhibition by soluble ligand in an IRBC-binding assay. The Sequestrin fusion protein GST-R(0–I) but not GST alone inhibited the binding of ItG (FIG. 6A) and 3D7 strains (not shown) of $P.$ $falciparum$ IRBC to purified CD36 in a dose-dependent manner. This inhibitory effect was specific for GST-R(0–I), since Sequestrin fusion proteins did not affect the binding of ItG-ICAM parasitized erythrocytes to purified ICAM-1 nor to thrombospondin (results not shown). Furthermore, Sequestrin protein fragments either expressed as fusion proteins with GST or purified by enzymatic cleavage of recombinant Sequestrin fragments with Factor Xa inhibited and reversed IRBC adhesion to C32 melanoma cells in vitro suggesting that the affinity of proteins R(0–I) and R(0–IV) for CD36 on the cell surface was sufficient to detach bound IRBC (FIG. 6B, FIGS. 7A, B). Fluorescent microspheres covalently linked to GST-R(0–I) decorated the surface of C32 melanoma cells (FIG. 7C) by binding to CD36 while C32 cells deficient in the surface expression of CD36 did not show any surface fluorescence.

Figure 8A:
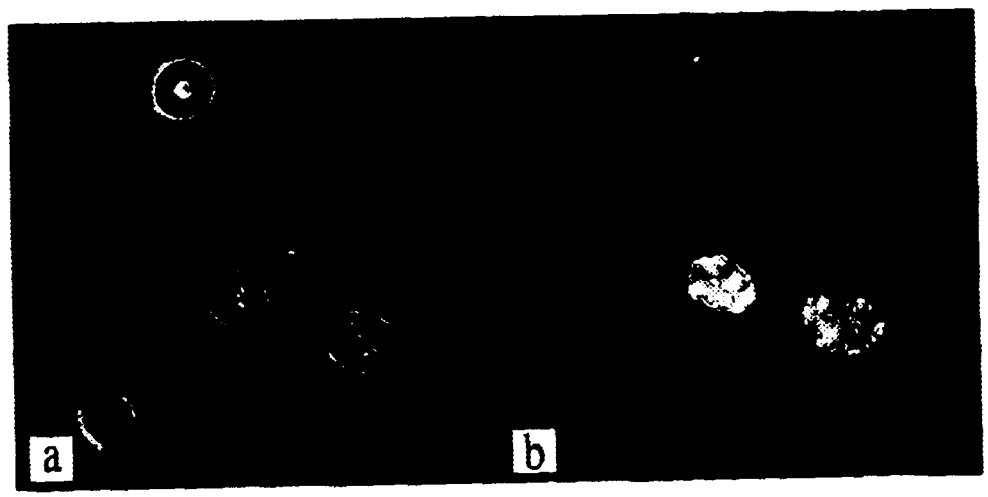
FIG. 8 shows antibodies against R(0–I) domain of Sequestrin react to surface of IRBC and inhibit binding to CD36. (A) Indirect immunofluorescene of intact unfixed IRBC incubated with rabbit anti-R(0–I) antisera demonstrates punctate surface staining. (B) Inhibition of IRBC binding to CD36 by rabbit anti-R(0–I) antiserum. Results are indicated as percent inhibition of quadruplicate samples compared to control samples (control binding, 3125 IRBC/mm2) incubated in the absence of sera.
Figure 8B:
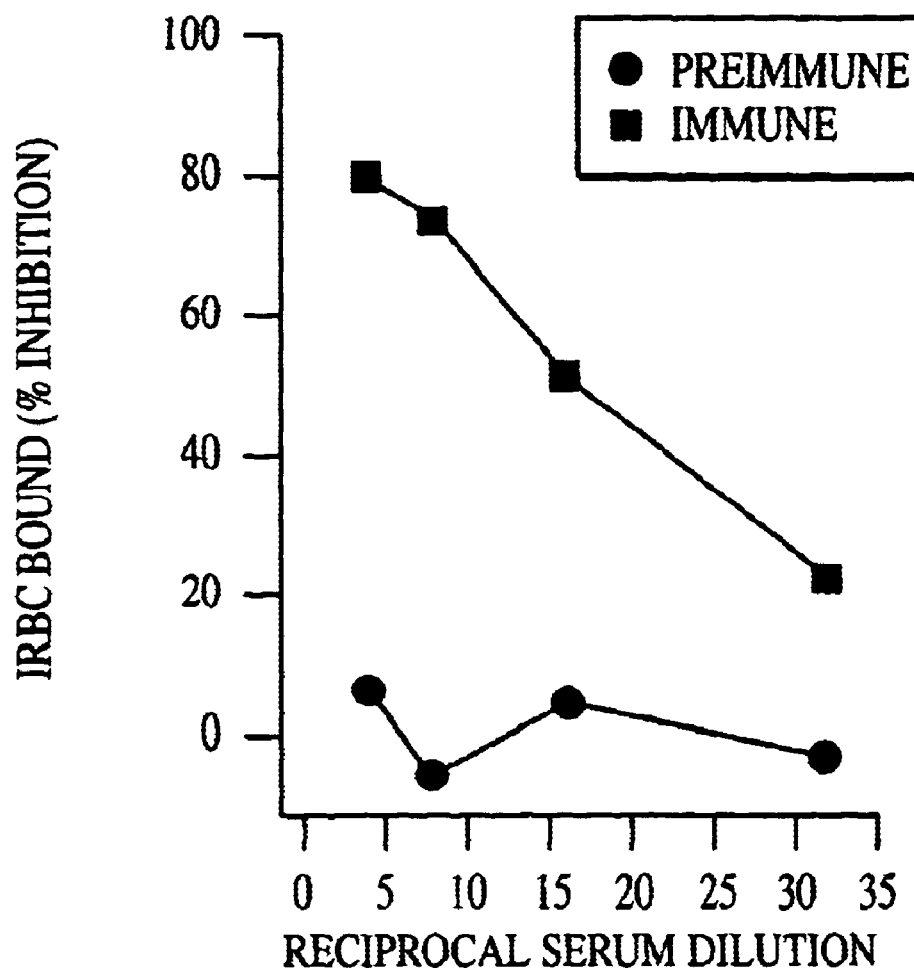

Polyclonal rabbit anti-Sequestrin R(0–I) antibodies both bound to the surface of live unfixed cytoadherent-positive parasitized erythrocytes by indirect fluorescent antibody staining (FIG. 8A) and inhibited IRBC binding to purified CD36 in a dose-dependent manner while pre-immune sera was without effect (FIG. 8B). This inhibitory effect was not detected in animals immunized with larger recombinant fusion proteins encompassing domains R(0–IV) although the end-point ELISA titers to domains R(0–I) and R(O–IV) were equivalent. The low titers required to achieve 50% inhibition (1:16) compared to high ELISA titers to overlapping Sequestrin recombinant proteins suggest that functional blocking antibodies against the CD36-binding domain on Sequestrin are either poorly immunogenic, inaccessible, or that the immune response is directed primarily to structually similar but non-functional immunodominant domains by epitope suppression of functionally relevant domains.

EXAMPLE 5

Figure 9:
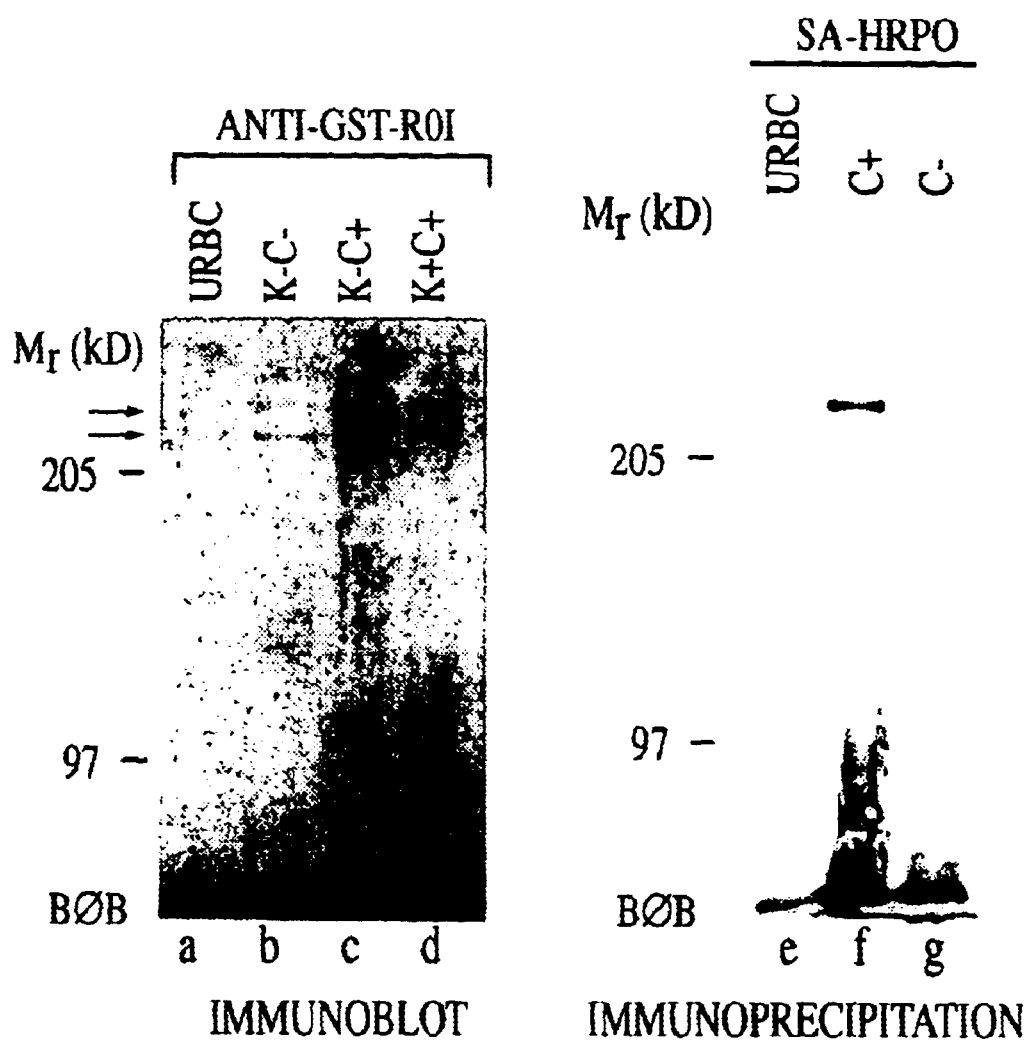
FIG. 9 shows that immunoblotting and immunoprecipitatin of cytoadherent and non-cytoadherent parasites with anti-Sequestrin antiserum identifies a high molecular weight protein. SDS extracts from uninfected erythrocytes (lane a), non-cytoadherent K-C- (lane b) or cytoadherent IRBC (lane c and d) were separated by SDS-PAGE, transferred to nitrocellulose membrane, and incubated with mouse anti-GST-R(0–I) antiserum. Bound antibodies were visualized by enhanced chemiluminescence (ECL). Arrows indicated the position of Sequestrin. For the immunoprecipitation experiment, parasitized erythrocytes were surface labeled with biotin, extracted with SDS, and extracts incubated with rabbit anti-R(0–I) antiserum. Immunoprecipitates were complexed with Protein A-Sepharose, washed, separated by SDS-PAGE, and transferred to nitrocellulose membrane. Surface-labeled proteins were detected by incubation of membranes with streptavidin-HRPO followed by ECL.

Antibodies Against Sequestrin Recognize a High Molecular Weight $P.$ $falciparum$ Protein Polyclonal rabbit antisera generated against Sequestrin R(0–I) was tested for reactivity by immunoblotting and immunoprecipitation to detergent extracts of $P.$ $falciparum$-infected erythrocytes. We hypothesized that non-cytoadherent parasites either would not express Sequestrin or express the protein at reduced levels compared to high levels of expression from wild-type parasites freshly adapted to human erythrocyte culture from Aotus-infected monkeys. Inasmuch as non-cytoadherent parasite lines adapted from either the ItG or 3D7 strains of $P.$ $falciparum$ have not been observed, we used cytoadherent and non-cytoadherent parasites from the Malayan Camp strain to precisely detect the molecular size of Sequestrin. Malayan Camp parasitized erythrocytes which bind poorly to both C32 cells and purified CD36 (MC $K^-C^-$) were maintained in continuous culture and selected to enrich a population of parasites which bind to CD36 (MC $K^-C^+$) according to a method previously described (Ockenhouse et al., 1991, supra). MC parasites from Aotus-infected monkeys and adapted to human erythrocyte culture retain both the knob and cytoadherence phenotypes (MCK$^+$C$^+$) and were used as a positive control. A high molecular weight protein doublet migrating at ~215–250 kD was identified by immunoblotting with mouse anti-R(0–I) antiserum in SDS-soluble extracts of cytoadherent MC $K^+C^+$ and $K^-C^+$ parasites but was absent from uninfected erythrocytes (FIG. 9). Low level reactivity was noted in total IRBC extracts from $K^-C^-$ parasites, suggesting that a small amount of Sequestrin exists in an intracellular pool some of which may be expressed at the red cell surface. This observation was not unexpected since cytoadherent-deficient parasites may be selected to bind CD36 by successive panning of parasites on immobilized CD36. Analogous high molecular weight protein bands were observed on immunoblots probed with affinity-purified rabbit anti-recombinant and anti-peptide sera prepared against non-overlapping Sequestrin peptide sequences or with affinity-purified OKM8 anti-idiotypic antibodies. On occasion, low level cross-reactivity with several parasite bands (~95, 150, 260, >300 kDa) were noted in immunoblots probed with some non-purified rabbit anti-Sequestrin antiserum representing cross-reactive antibodies against highly immunoreactive diglutamic acid (E—E) repeat sequences. These cross-reactive antigens were not present on immunoblots probed with antiserum affinity-purified against synthetic Sequestrin peptides lacking diglutamic acid motifs.

As expected, anti-R(0–I) antisera immunoprecipitated an identical protein doublet from surface biotinylated cytoadherent positive IRBC but not from cytoadherent deficient IRBC or from uninfected red blood cells (FIG. 9). The pre-bleed sera from the immunized rabbit or a monoclonal antibody against GST did not immunoprecipitate the >200 kD proteins indicating that the antibodies elicited in response to immunization with the CD36-binding domain GST-R(0–I) are specific for Sequestrin. Since the treatment of infected erythrocytes with low concentrations of trypsin abolishes cytoadherence to cells expressing CD36 (Leech et al. (1984) $J.$ $Exp.$ $Med.$ 159: 1567–1575), we pre-incubated surface-labeled IRBC with trypsin (10 mg/ml for 10 minutes at room temperature) prior to detergent extraction and immunoprecipitation with anti-R(0–I) antibodies (results not shown). No erythrocyte surface labeling of Sequestrin was detected under these conditions demonstrating that Sequestrin (Ockenhouse et al., 1991, supra) like PfEMP1 (Baruch et al. (1995) Cell 82: 77–87) and modified erythrocyte Band 3 (Winograd and Sherman (1989) $Biochem.$ $Biophys.$ $Res.$ $Commun.$ 160: 1357–1363) expressed on the infected erythrocyte surface is trypsin sensitive. These immunoblotting and immunoprecipitation experiments using recombinant antiserum support our previous findings that immunoprecipitation with CD36-specific anti-idiotype antiserum identifies a high (>200 kD) molecular weight parasite-derived surface protein(s) from cytoadherent *P. falciparum*-infected red blood cells as Sequestrin (Ockenhouse et al., 1991, supra). Whether the protein doublet repesents a precursor and processed form of Sequestrin or proteolytic cleavage of a single molecular species after detergent extraction is not known. The full molecular characterization of Sequestrin must await sequencing and analysis of the entire molecule.

A number of independent modalities provide direct evidence that the protein Sequestrin identified by expression-cloning binds to CD36: 1) CD36 binds to several recombinant constructs of the protein or its fragments expressed with three different fusion partners, but only to those fragments containing the specific binding domain, R(0 –1), in amino acids H42-M168; 2) Radiolabelled CD36 adheres to recombinant fragments containing R(0–1) which have undergone PAGE fractionation and blotting onto a nitrocellulose membrane; 3) Labelled CD36 also adheres to recombinant forms of the binding domain bound to plastic in a microtiter format; this binding is dose-dependent, and is competitively inhibited by unlabelled CD36. CD36 does not adhere to control proteins using the same formats; 4) Recombinant Sequestrin inhibits and reverses binding of IRBC both to CD36 and to C32 melanoma cells (which express CD36). The direct data using purified proteins is corroborated by antibody data. Rabbit antisera raised against R(0–1) reacts with live IRBC in IFA, as expected with a surface protein such as sequestrin. In binding assays, this antisera, like the recombinant protein, is able to inhibit the adhesion of IRBC to purified CD36; preimmune sera fails to inhibit.

Antibodies against R(0–1) recognize two bands greater than 200 kD in a immunoblot and immunoprecipitation of IRBC extracts. These bands are not recognized in extracts of uninfected RBC, and the size of these bands does not vary between different parasite isolates. The Mr of these bands corresponds to those recognized by anti-idiotypic antibodies raised against OKM8, the anti-CD36 mAb which inhibits IRBC binding to CD36; these anti-idiotypic antibodies were previously used to establish the antigenic identity of Sequestrin (Ockenhouse et al., 1991, supra). Further, in a competitive binding assay, binding of CD36 to R(0–1) was inhibited by OKM8, but not by anti-CD36 mAbs M030 and M052 (which do not inhibit IRBC binding to CD36), demonstrating the fine specificity in the interaction between Sequestrin and CD36. These data indicate that the binding domain identified by expression-cloning shares identity with Sequestrin, and, together with nucleotide sequence data, distinguish sequestrin from erythrocyte band 3 and PfEMP1, two other putative cytoadherence receptors.

All field isolates of *P. falciparum* bind to CD36, while smaller proportions bind to other ligands such as ICAM-1, VCAM-1, and E-selectin (Ockenhouse et al., 1992, supra). The potential to bind multiple receptors offers redundancy to the vital mechanism of cytoadherence, and the phenotypic heterogeneity may account for the spectrum of clinical syndromes associated with malaria. Binding to a particular receptor(s), for example, may be associated with the development of cerebral malaria. However, the ubiquity of the CD36-binding phenotype among field isolates suggests that this characteristic may be essential to the survival of the organism in nature, and is associated with the expression of Sequestrin. By serial panning over CD36, a population of adherent parasites can be selected from previously noncytoadherent MC parasites; this shift in phenotype is accompanied by a significant increase in the expression of Sequestrin, which is nearly absent in extracts of noncytoadherent parasites.

The essential role of Sequestrin for parasite survival entails that the organism develop mechanisms for evading host immunologic recognition, particularly from humoral interference with adhesion. The amino acid sequence in the CD36-binding domain is conserved among several field isolates from widely disparate geographic locations, suggesting that antigenic variation within the biologically functional segment of the protein is not the mechanism of evasion. Conversely, the E—E pair repeated 6 times in R(0–1) is present in several other malaria proteins, including RESA/Pf150, Ag332, Pf11.1, Pf270, and GLURP and are critical residues for recognition by human monoclonal antibody 33G2 which is cross-reactive with these proteins. Immunization with R(0–1) elicits antisera which reacts not only with the original immunogen, but also with R3, a downstream fragment which contains 7 repeats of the diglutamic acid pair. Thus, "decoy epitopes" within Sequestrin or other malaria proteins may divert antibodies away from adhesion domains to biologically non-functional protein segments.

Identification of the CD36-binding domain of Sequestrin offers great promise for the development of malaria therapeutics in the form of vaccines or adhesion inhibitors. Because the amino acid sequence is highly conserved within this domain, immunogens or analogs are likely to be broadly effective among different parasite strains. Fine specification of the residues involved in binding to CD36 would allow the design of immunogens without the immunodominant epitopes which divert antibodies to non-functional protein segments. Finally, as other proteins are substantiated to be parasite adhesion molecules, the complex phenomenon of parasite sequestration and its role in disease pathology can be dissected.

What is claimed is:

1. An isolated peptide consisting of the amino acid sequence specified in SEQ ID NO:2, or a portion thereof which comprises at least 8 contiguous amino acids, wherein the peptide or portion thereof binds specifically to CD36.

2. A peptide of claim 1, wherein said portion comprises at least 12 contiguous amino acids.

3. A peptide of claim 1, which consists of the amino acid sequence specified in SEQ ID NO:2.

4. An immunogenic composition comprising a peptide or portion thereof of claim 1.

5. A method to elicit an immune response in a mammal, comprising administering to said mammal an effective amount of a peptide or portion thereof of claim 4.

6. An isolated peptide consisting of the amino acid sequence specified in SEQ ID NO:2, or a portion thereof which comprises at least 10 contiguous amino acids.

7. An immunogenic composition comprising a peptide or portion thereof of claim 6.

8. An isolated peptide consisting of the amino acid sequence specified in SEQ ID NO:4, or a portion thereof which comprises at least 8 contiguous amino acids, wherein the peptide or portion thereof binds specifically to CD36.

9. A peptide of claim 8, wherein said portion comprises at least 12 contiguous amino acids.

10. A peptide of claim 8, which consists of the amino acid sequence specified in SEQ ID NO:4.

11. An immunogenic composition comprising a peptide or portion thereof of claim 8.

12. An isolated peptide consisting of the amino acid sequence specified in SEQ ID NO:4, or a portion thereof which comprises at least 10 contiguous amino acids.

13. An immunogenic composition comprising a peptide or portion thereof of claim 12.

14. A method to elicit an immune response in a mammal, comprising administering to said mammal an effective amount of a peptide or portion thereof of claim 13.

* * * * *